(12) United States Patent
Lee et al.

(10) Patent No.: US 10,344,028 B2
(45) Date of Patent: Jul. 9, 2019

(54) ORGANIC SEMICONDUCTOR COMPOUND, PRODUCTION METHOD THEREOF, AND ORGANIC ELECTRONIC DEVICE USING THE SAME

(71) Applicants: Korea Research Institute of Chemical Technology, Yuseong-gu, Daejon (KR); Kyonggi University Industry & Academia Cooperation Foundation, Suwon-si, Gyeonggi-do (KR)

(72) Inventors: Jong Cheol Lee, Seoul (KR); Sang Kyu Lee, Daejeon (KR); Won Suk Shin, Daejeon (KR); ChangEun Song, Busan (KR); Sang Jin Moon, Daejeon (KR); Hang Ken Lee, Daejeon (KR); Eunhee Lim, Seoul (KR)

(73) Assignees: Korea Research Institute of Chemical Technology (KR); Kyonggi University Industry & Academia Cooperation Foundation (KR)

( * ) Notice: Subject to any disclaimer, the term of this patent is extended or adjusted under 35 U.S.C. 154(b) by 0 days.

(21) Appl. No.: 15/964,451

(22) Filed: Apr. 27, 2018

(65) Prior Publication Data

US 2019/0040056 A1 Feb. 7, 2019

(30) Foreign Application Priority Data

Aug. 3, 2017 (KR) ........................ 10-2017-0098500

(51) Int. Cl.
*C07D 421/14* (2006.01)
*C07D 417/14* (2006.01)
*H01L 51/00* (2006.01)
*H01L 51/42* (2006.01)

(52) U.S. Cl.
CPC .......... *C07D 421/14* (2013.01); *C07D 417/14* (2013.01); *H01L 51/0069* (2013.01); *H01L 51/4253* (2013.01)

(58) Field of Classification Search
CPC ........................... C07D 421/14; C07D 417/14
See application file for complete search history.

(56) References Cited

U.S. PATENT DOCUMENTS

2006/0011233 A1  1/2006  Sariciftci et al.

FOREIGN PATENT DOCUMENTS

KR    10-2016-0011039 A    1/2016

OTHER PUBLICATIONS

Office Action dated Sep. 17, 2018, in KR Application No. 10-2017-0098500.
Li et al., "Solution Processable Rhodanine-Based Small Molecule Organic Photovoltaic Cells with a Power Conversion Efficiency of 6.1%," Advanced Energy Materials, 2012, 2:74-77.
Ni et al., "A-D-A small molecules for solution-processed organic photovoltaic cells," Chem. Commun., 2015, 51:4936-4950.

*Primary Examiner* — Rebecca L Anderson
(74) *Attorney, Agent, or Firm* — Foley & Lardner LLP

(57) ABSTRACT

Provided are a novel organic semiconductor compound, a production method thereof, and an organic electronic device using the same, wherein the organic semiconductor compound includes a thiazolidine functional group introduced into a heteroaromatic ring to thereby remarkably improve photovoltaic characteristics of an organic electronic device including the same.

10 Claims, No Drawings

ORGANIC SEMICONDUCTOR COMPOUND, PRODUCTION METHOD THEREOF, AND ORGANIC ELECTRONIC DEVICE USING THE SAME

CROSS-REFERENCE TO RELATED APPLICATIONS

This application claims priority under 35 U.S.C. § 119 to Korean Patent Application No. 10-2017-0098500, filed on Aug. 3, 2017, in the Korean Intellectual Property Office, the disclosure of which is incorporated herein by reference in its entirety.

TECHNICAL FIELD

The following disclosure relates to a novel organic semiconductor compound and an organic electronic device using the same, and more particularly, to an organic semiconductor compound in which a thiazolidine functional group is introduced into a heteroaromatic ring compound as a central backbone, a production method thereof, and an organic electronic device using the same.

BACKGROUND

An organic thin film solar cell is a device using a donor material and an acceptor material together for a photoactive layer, and has advantages in that as compared to conventional inorganic semiconductor devices, a film forming condition is not complicated, and a material of a photoactive layer having a thin thickness of several hundreds of nanometers or less and being relatively inexpensive, in particular, a flexible device that is bendable freely, is capable of being produced. Thus, a number of researches on the organic thin film solar cell are underway.

The organic thin film solar cell has a bonding structure of an electron donor and an electron acceptor, and exhibits a very rapid charge transfer phenomenon which is so-called "photoinduced charge transfer (PICT)" between the electron donor and the electron acceptor, i.e., a photovoltaic effect.

When an organic semiconductor compound used as the electron donor is a semiconductor polymer, various derivatives of a poly para-phenylenevinylene (hereinafter referred to as "PPV")-based material and polythiophene (hereinafter referred to as "PT") are used. Further, C60 fullerene itself or a C60 fullerene derivative designed to easily dissolve C60 fullerene in an organic solvent is used as the electron acceptor, and perylene, 3,4,9,10-perylene tetra carboxylic acid diimide, phthalocyanine, pentacene, etc., are used as other small molecules.

In order to increase efficiency of the solar cell, a contact area between the electron donor and the electron acceptor should be large, and two separated charges should be movable to an electrode without loss of charge.

Thus, researches on various electron donors are underway. For example, U.S. Patent Application Publication No. 2006-0011233 describes an organic photovoltaic device in which poly (3-hexylthiophene) (P3HT) is used as an electron donor, [6,6]-phenyl-C61-butyric acid methyl ester (C60-PCMB) is used as an electron acceptor, and a photoelectric conversion layer is introduced by a spin coating method.

Up to now, a research on an electron donor has been numerously conducted, but a research on a compound for replacing a fullerene derivative used as the electron acceptor has been hardly conducted.

Since a large number of fullerene derivatives have low solubility with respect to an organic solvent, a phase separation phenomenon occurs when mixed with a polymer, and thus an efficiency in view of an appearance is generally low, light absorption with respect to a range of a region at which solar spectrum is strong is weak, an operation for energy level is difficult, and miscibility with the electron donor is low. Thus, a research on a compound for replacing fullerene is urgently needed.

Specifically, as the compound for replacing the fullerene derivative, a compound having high electron affinity similar to that of fullerene while simultaneously having excellent miscibility with the electron donor, high absorption coefficient, and excellent photo conversion efficiency, is required to be studied.

SUMMARY

An embodiment of the present disclosure is directed to providing a novel organic semiconductor compound, and a production method thereof.

Another embodiment of the present disclosure is directed to providing an organic electronic device using the organic semiconductor compound.

In one general aspect, there is provided an organic semiconductor compound having a high light absorption coefficient and high charge mobility and excellent miscibility with an electron donor, wherein the organic semiconductor compound is represented by Chemical Formula 1 below:

[Chemical Formula 1]

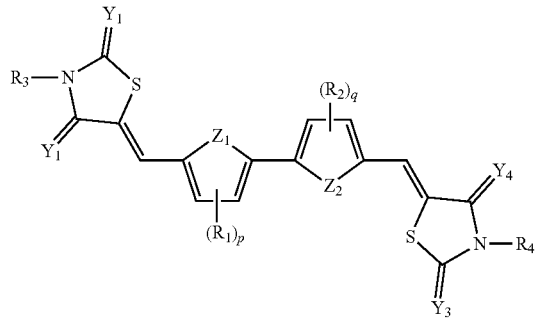

in Chemical Formula 1, $Z_1$ and $Z_2$ are each independently O, S, or Se;

$Y_1$ to $Y_4$ are each independently O, S, Se or $CR^aR^b$, and $R^a$ and $R^b$ are each independently cyano, a carboxyl group, (C1-C20)alkyl, (C1-C20)alkoxy or (C1-C20)alkoxycarbonyl;

$R_1$ and $R_2$ are each independently halogen, (C1-C20)alkyl, halo(C1-C20)alkyl, (C1-C20)alkoxy, (C1-C20)alkylthio, (C1-C20)alkoxycarbonyl or (C6-C20)ar(C1-C20)alkyl;

p and q are each independently 0 or an integer of 1 to 2, and when p and q are 2, $R_1$ and $R_2$ each may be the same as or different from each other; and $R_3$ and $R_4$ are each independently hydrogen or (C1-C20)alkyl.

Preferably, in Chemical Formula 1 according to an exemplary embodiment of the present disclosure, $Z_1$ and $Z_2$ are equally O, S, or Se; $Y_1$ to $Y_4$ are each independently O, S or Se; $R_1$ and $R_2$ are each independently halogen, (C1-C20)alkyl, halo(C1-C20)alkyl or (C1-C20)alkoxycarbonyl; p and q are each independently 0 or an integer of 1 to 2, and when p and q are 2, $R_1$ and $R_2$ each may be the same as or different from each other; and $R_3$ and $R_4$ may be each independently (C1-C20)alkyl.

In order to achieve an excellent light absorption coefficient, miscibility with an electron donor, and photoelectric conversion efficiency, preferably, $Y_1$ and $Y_2$ may be different from each other, and $Y_3$ and $Y_4$ may be different from each other, and more preferably, the organic semiconductor compound of the present disclosure may be represented by Chemical Formula 2 below:

[Chemical Formula 2]

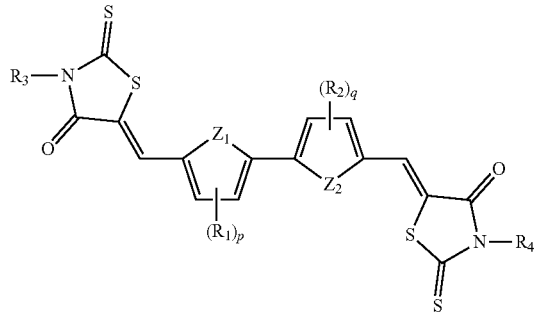

in Chemical Formula 2, $Z_1$ and $Z_2$ are each independently O, S, or Se;

$R_1$ and $R_2$ are each independently halogen, (C1-C20)alkyl, halo(C1-C20)alkyl or (C1-C20)alkoxycarbonyl;

p and q are each independently 0 or an integer of 1 to 2, and when p and q are 2, $R_1$ and $R_2$ each may be the same as or different from each other; and $R_3$ and $R_4$ are each independently (C1-C20)alkyl.

Preferably, $Z_1$ and $Z_2$ in the organic semiconductor compound according to an exemplary embodiment of the present disclosure may be equally O, S, or Se.

In an exemplary embodiment of the present disclosure, the organic semiconductor compound may be selected from the following compounds, but is not limited thereto:

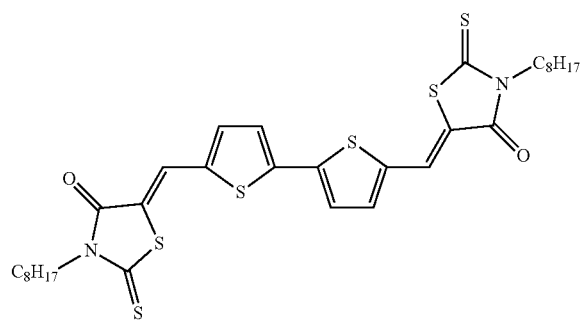

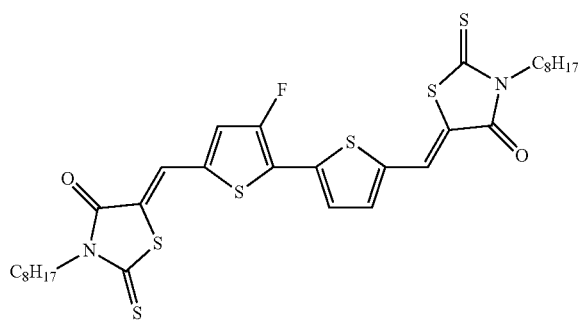

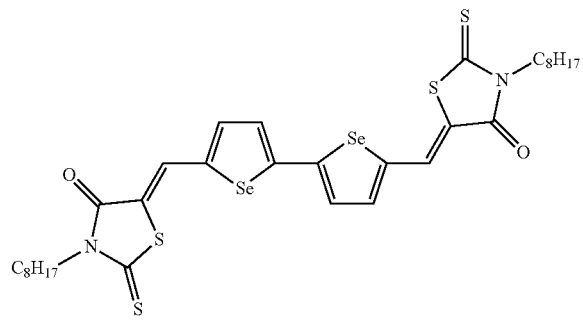

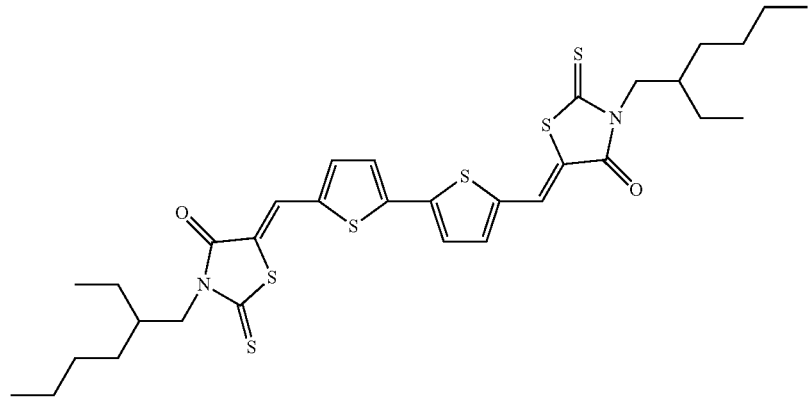 [SMILES: CCCCC(CC)CN1C(=O)/C(=C/c2ccc(-c3ccc(/C=C4\SC(=S)N(CC(CC)CCCC)C4=O)s3)s2)SC1=S]

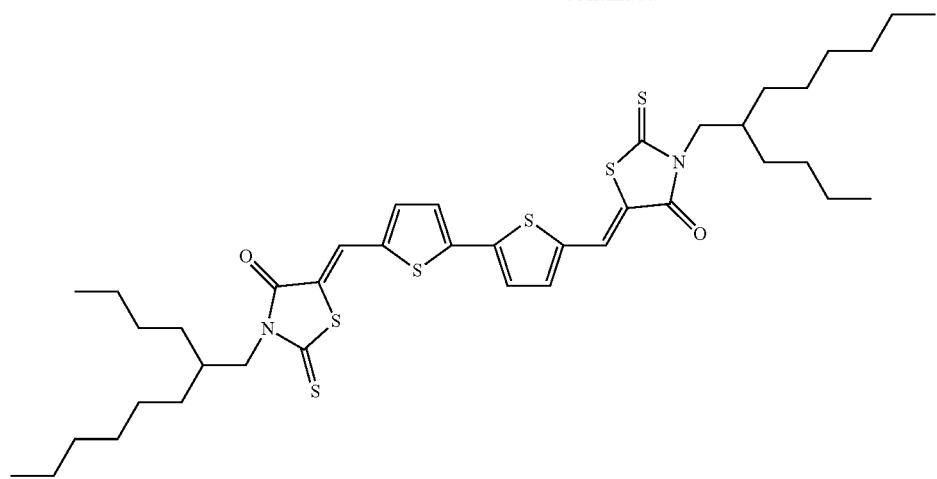
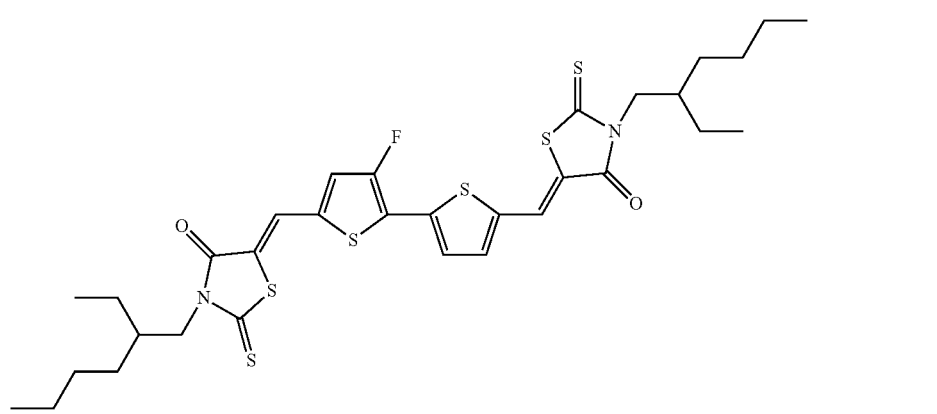 [SMILES: CCCCC(CC)CN1C(=O)/C(=C/c2ccc(-c3sc(/C=C4\SC(=S)N(CC(CC)CCCC)C4=O)cc3F)s2)SC1=S]
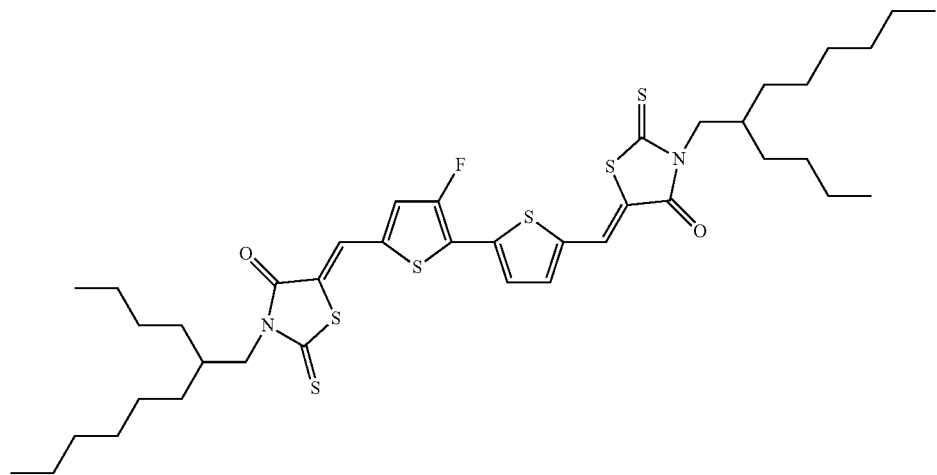 [SMILES: CCCCCCC(CCCC)CN1C(=O)/C(=C/c2ccc(-c3sc(/C=C4\SC(=S)N(CC(CCCC)CCCCCC)C4=O)cc3F)s2)SC1=S]
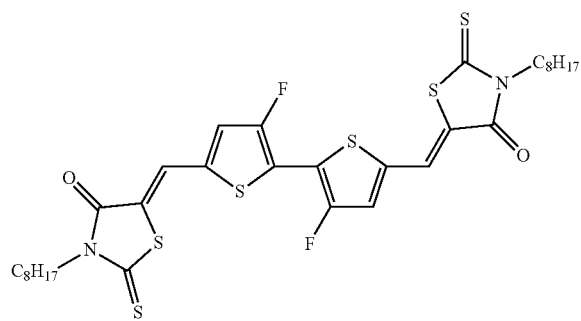

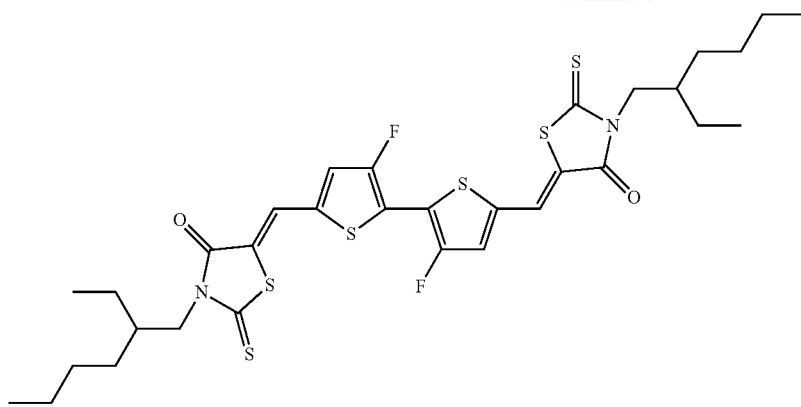
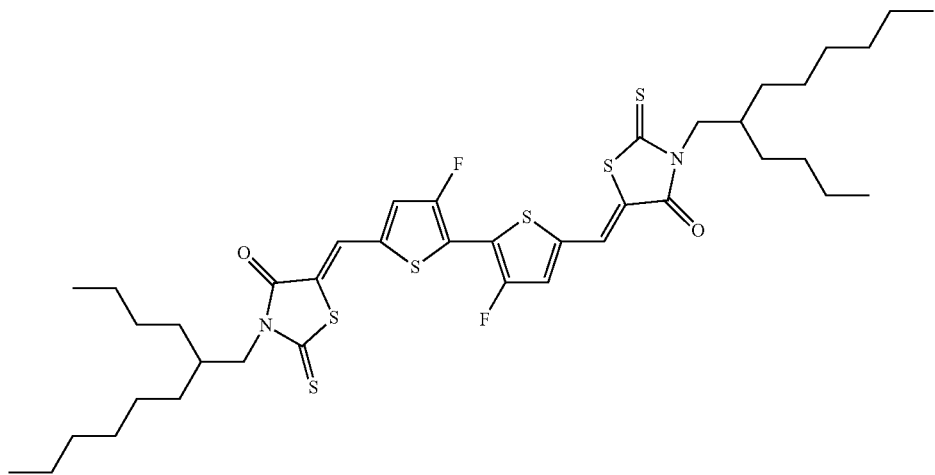 [SMILES: CCCCCCC(CCCC)CN1C(=O)/C(=C/c2cc(F)c(-c3sc(/C=C4\SC(=S)N(CC(CCCC)CCCCCC)C4=O)cc3F)s2)SC1=S]
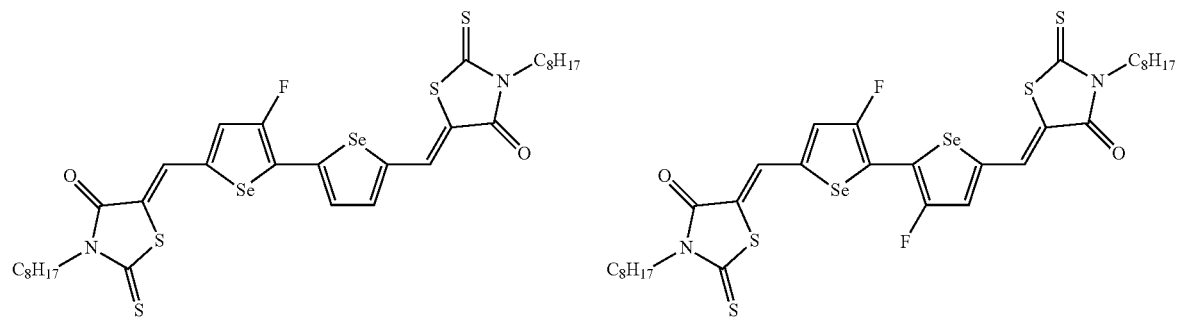
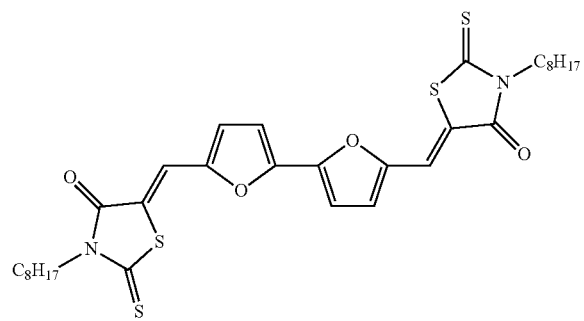

-continued
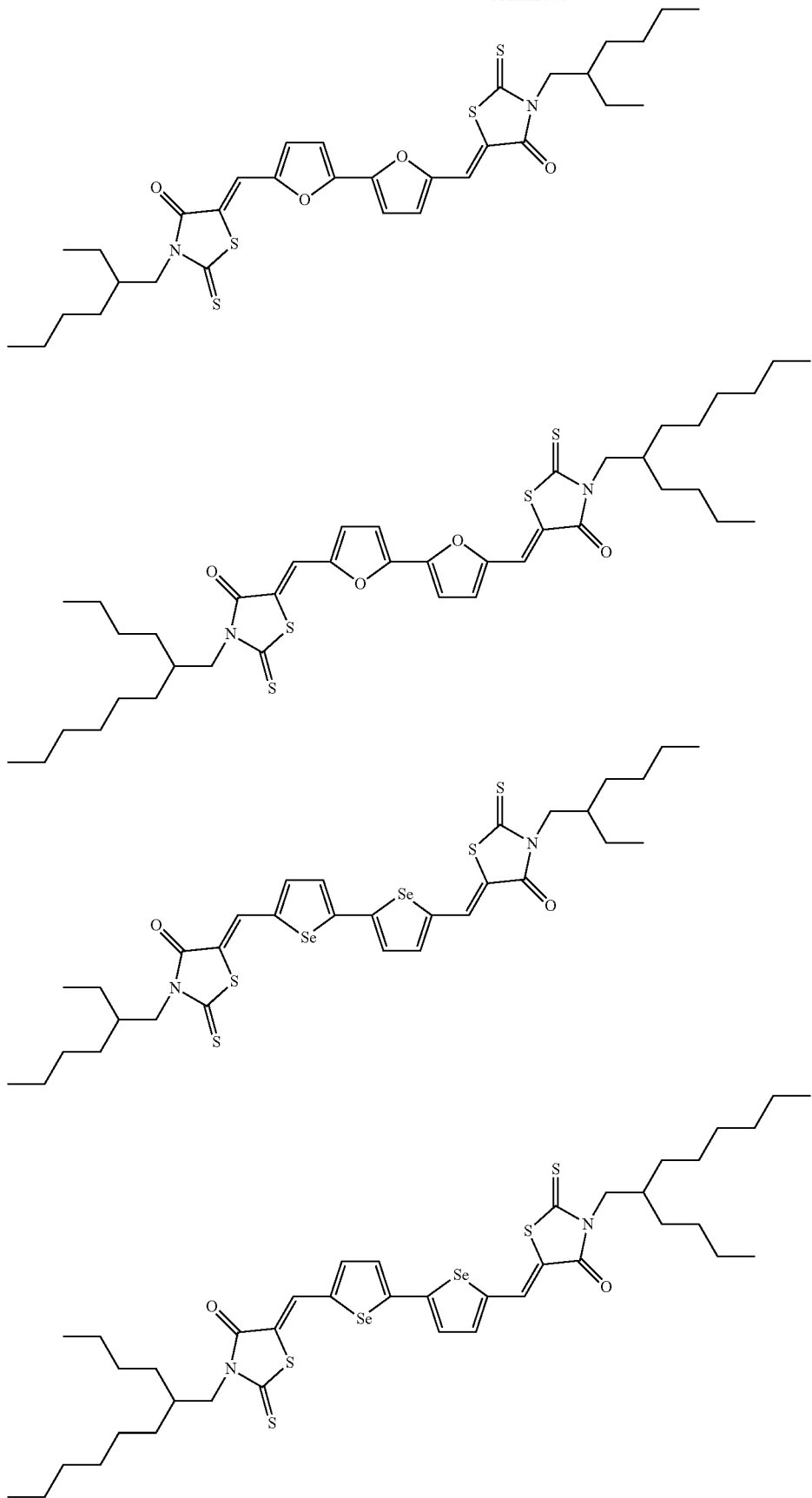

-continued
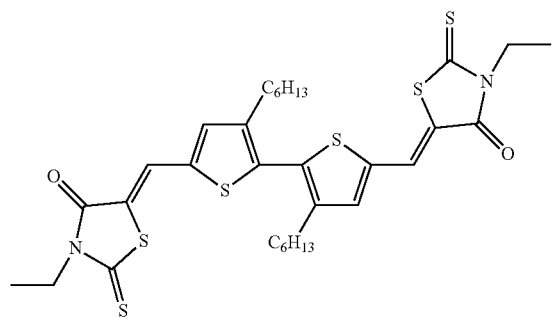
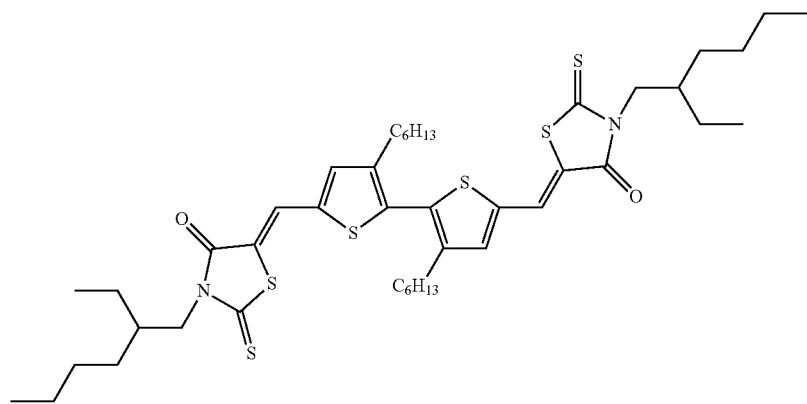
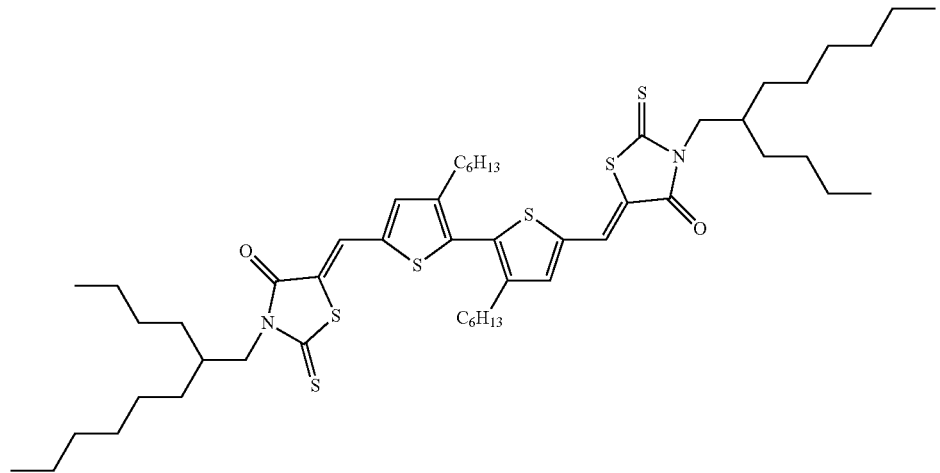
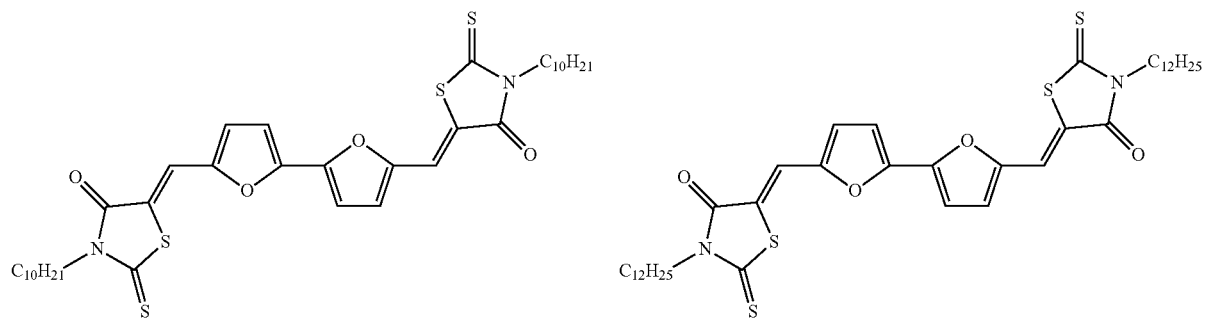

-continued
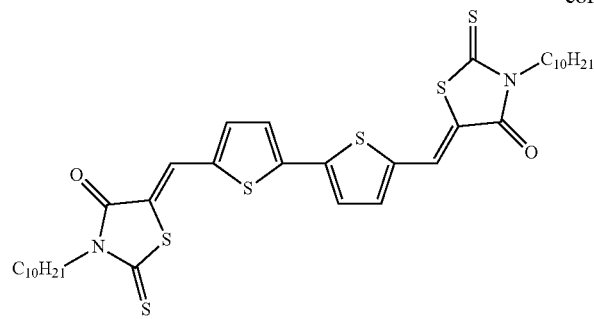
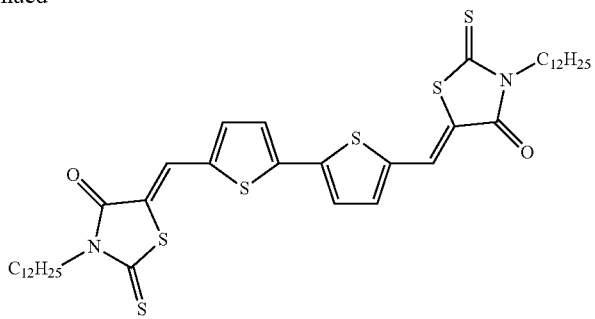
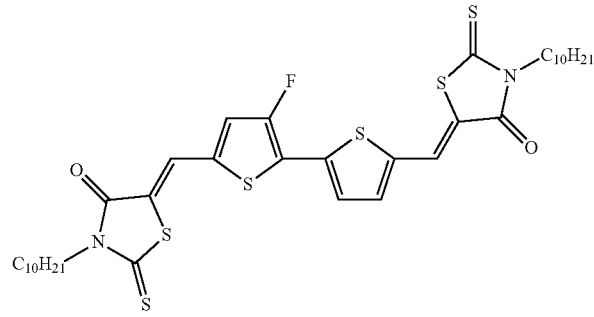
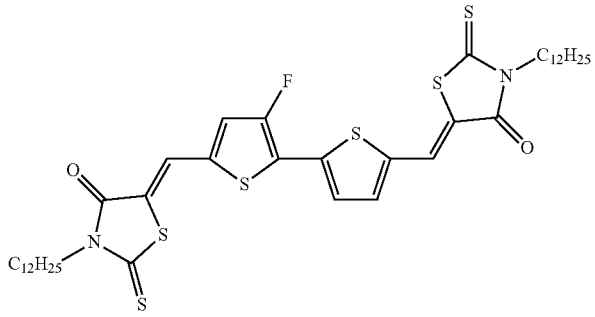
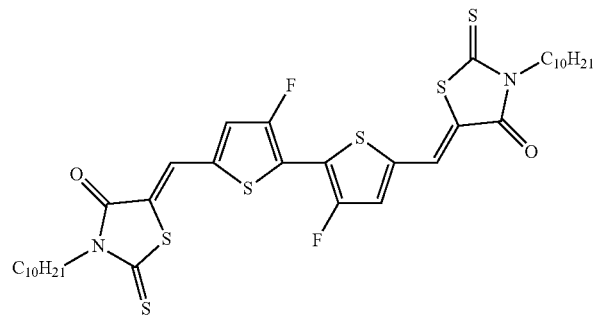
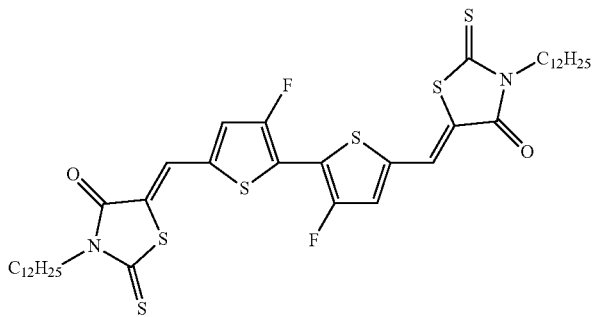
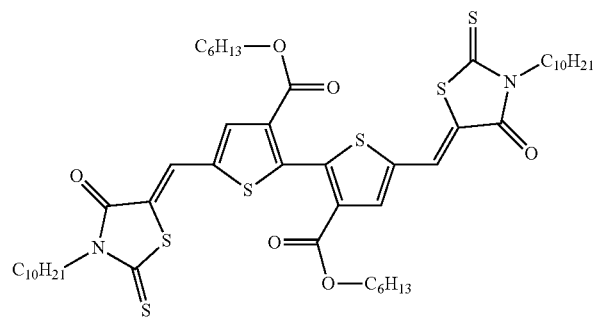
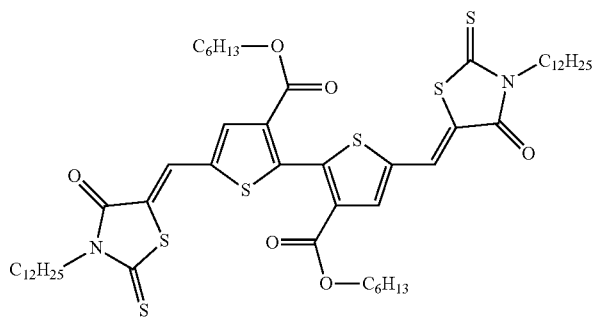
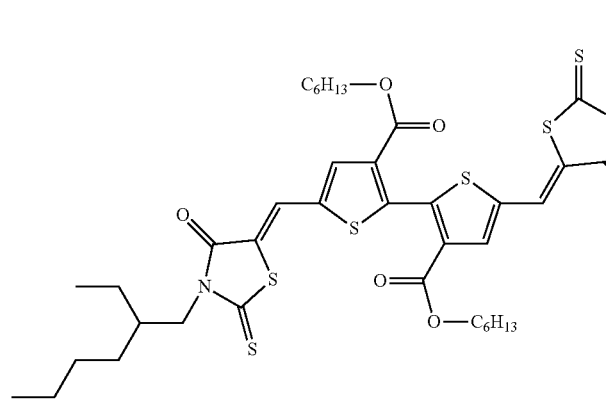
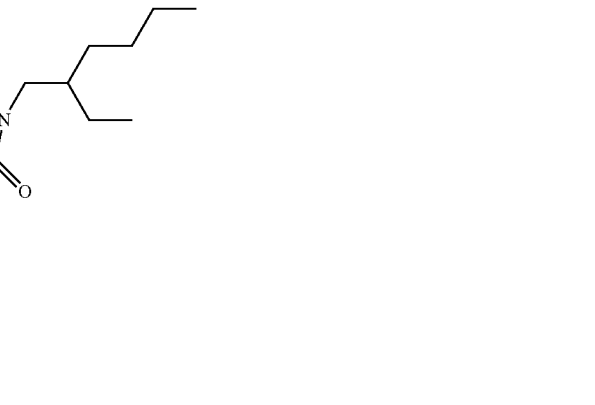

-continued
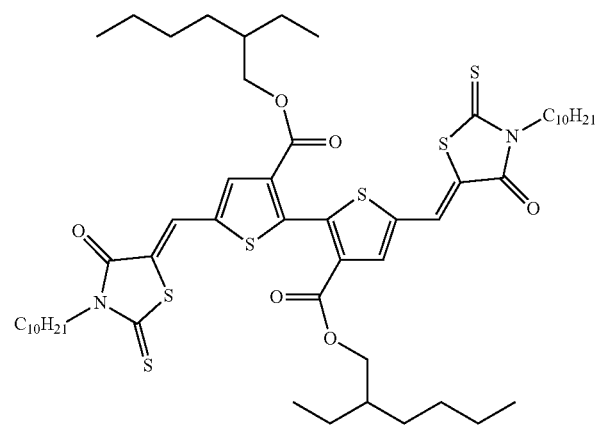
15
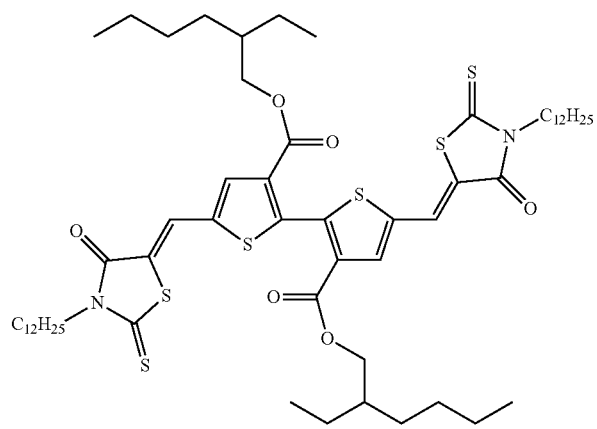
16
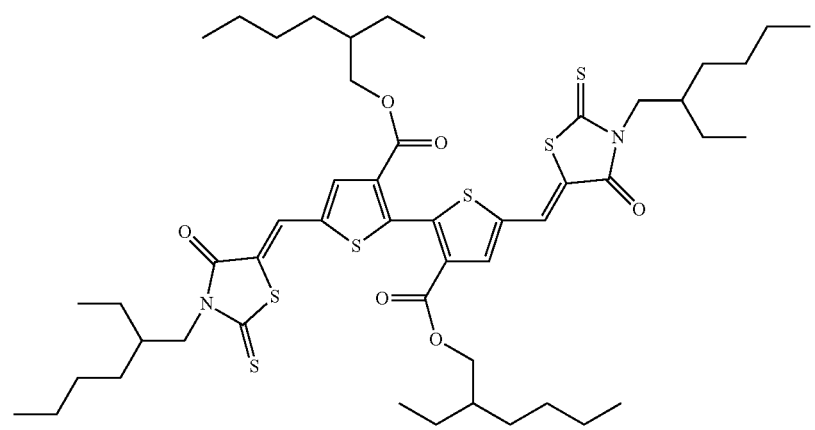
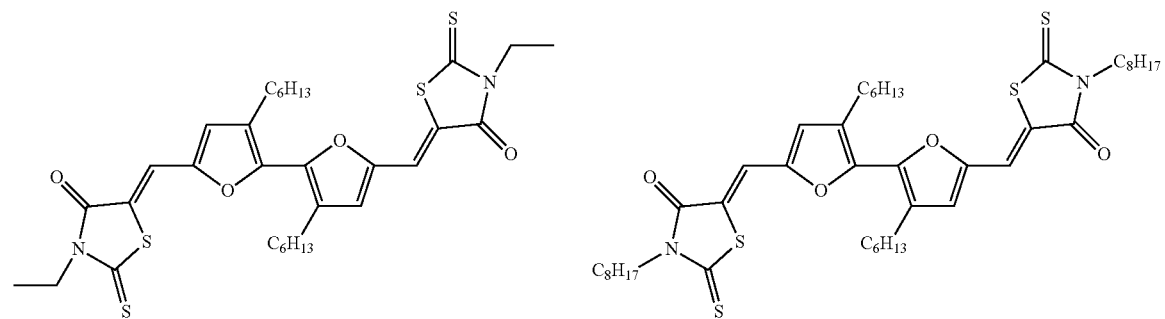
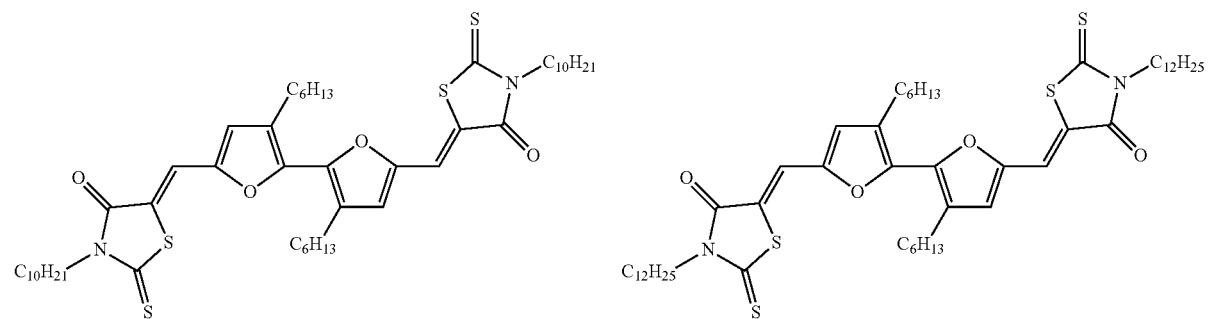

17
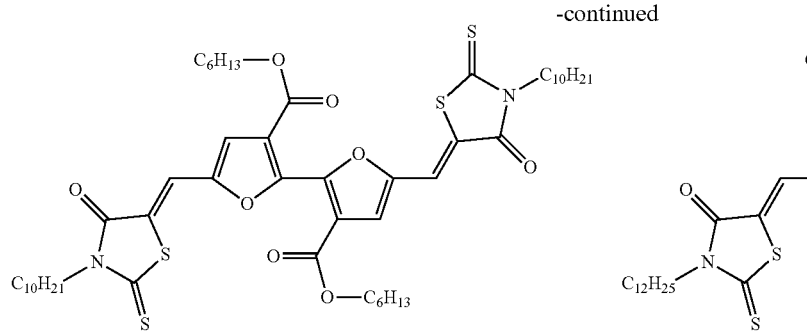
18
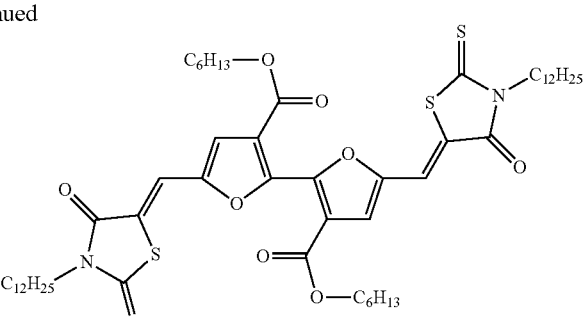
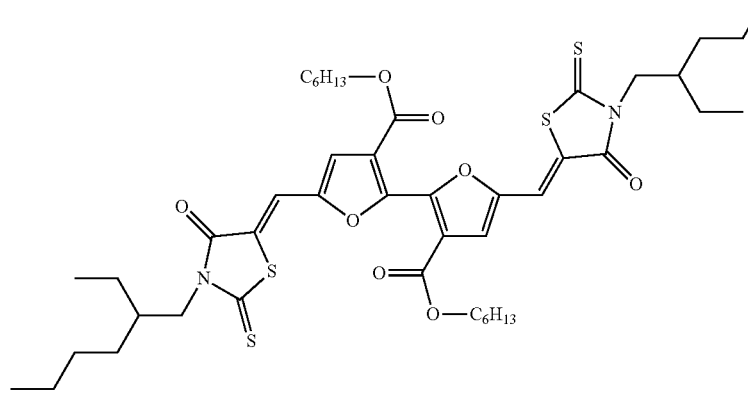
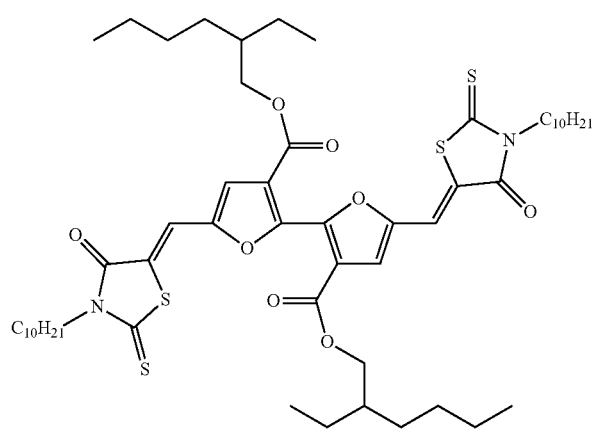
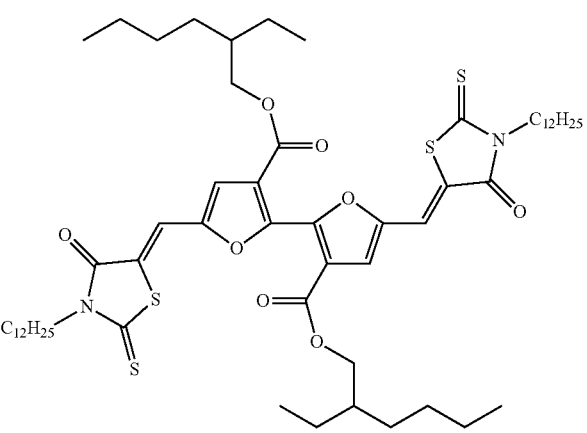
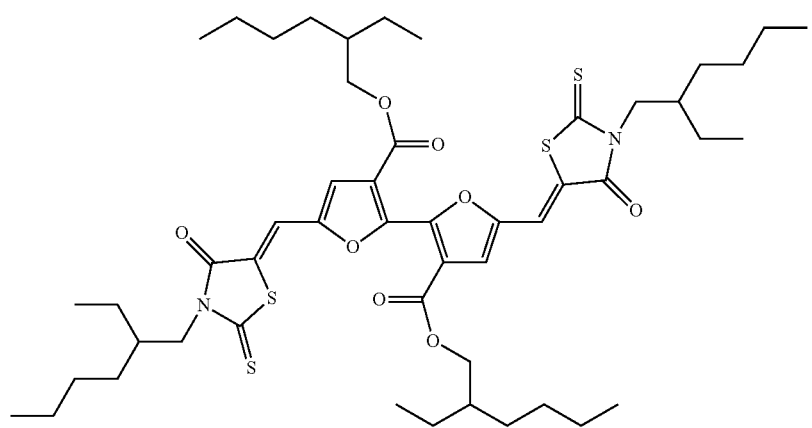

In another general aspect, there is provided a production method of the organic semiconductor compound represented by Chemical Formula 1 of the present disclosure, including producing the organic semiconductor compound represented by Chemical Formula 1 above by reacting a dicarbaldehyde compound represented by Chemical Formula 3 below, a thiazolidine compound represented by Chemical Formula 4 below, and a thiazolidine compound represented by Chemical Formula 5 below:

[Chemical Formula 3]

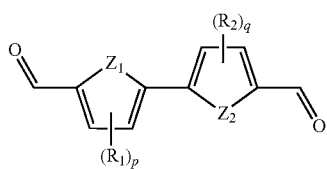

[Chemical Formula 4]

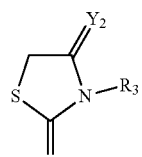

[Chemical Formula 5]

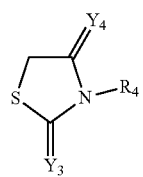

in Chemical Formulas 3 to 5, $Z_1$ and $Z_2$ are each independently O, S, or Se;

$Y_1$ to $Y_4$ are each independently O, S, Se or $CR^aR^b$, and $R^a$ and $R^b$ are each independently cyano, a carboxyl group, (C1-C20)alkyl, (C1-C20)alkoxy or (C1-C20)alkoxycarbonyl;

$R_1$ and $R_2$ are each independently halogen, (C1-C20)alkyl, halo(C1-C20)alkyl, (C1-C20)alkoxy, (C1-C20)alkylthio, (C1-C20)alkoxycarbonyl or (C6-C20)ar(C1-C20)alkyl;

p and q are each independently 0 or an integer of 1 to 2, and when p and q are 2, $R_1$ and $R_2$ each may be the same as or different from each other; and $R_3$ and $R_4$ are each independently hydrogen or (C1-C20)alkyl.

In still another general aspect, there is provided an organic electronic device including the organic semiconductor compound as described above.

The organic electronic device may be an organic solar cell.

The organic semiconductor compound may be included in a photoactive layer of the organic solar cell.

The organic semiconductor compound may be included as an electron acceptor in a photoactive layer of the organic solar cell.

DETAILED DESCRIPTION OF EMBODIMENTS

The present disclosure provides a novel organic semiconductor compound that is useful as various photoelectric conversion materials, wherein the organic semiconductor compound is represented by Chemical Formula 1 below:

[Chemical Formula 1]

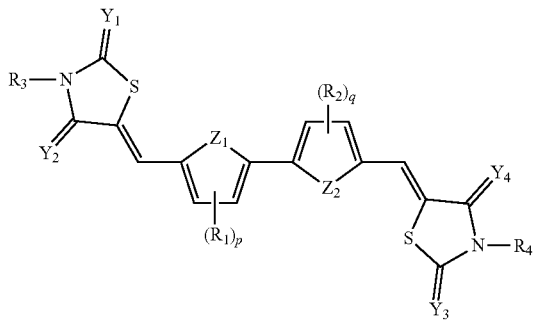

in Chemical Formula 1, $Z_1$ and $Z_2$ are each independently O, S, or Se;

$Y_1$ to $Y_4$ are each independently O, S, Se or $CR^aR^b$, and $R^a$ and $R^b$ are each independently cyano, a carboxyl group, (C1-C20)alkyl, (C1-C20)alkoxy or (C1-C20)alkoxycarbonyl;

$R_1$ and $R_2$ are each independently halogen, (C1-C20)alkyl, halo(C1-C20)alkyl, (C1-C20)alkoxy, (C1-C20)alkylthio, (C1-C20)alkoxycarbonyl or (C6-C20)ar(C1-C20)alkyl;

p and q are each independently 0 or an integer of 1 to 2, and when p and q are 2, $R_1$ and $R_2$ each may be the same as or different from each other; and $R_3$ and $R_4$ are each independently hydrogen or (C1-C20)alkyl.

The organic semiconductor compound represented by Chemical Formula 1 of the present disclosure has a wide absorption spectrum in a panchromatic region, excellent light absorption, and a low lowest unoccupied molecular orbital energy level (LUMO) to be very efficiently usable as an electron acceptor by introducing a thiazolidine functional group into a heteroaryl central backbone, specifically, a 5-membered heteroaromatic ring.

Further, the organic semiconductor compound represented by Chemical Formula 1 of the present disclosure has a high crystallinity to have high charge mobility. In particular, the organic semiconductor compound is used as a compound for replacing a fullerene derivative according to the related art, thereby having high electron affinity while simultaneously having excellent miscibility with the electron donor to have high photoelectric conversion efficiency.

Preferably, in Chemical Formula 1 according to an exemplary embodiment of the present disclosure, $Z_1$ and $Z_2$ are equally O, S, or Se; $Y_1$ to $Y_4$ are each independently O, S or Se; $R_1$ and $R_2$ are each independently halogen, (C1-C20)alkyl, halo(C1-C20)alkyl or (C1-C20)alkoxycarbonyl; p and q are each independently 0 or an integer of 1 to 2, and when p and q are 2, $R_1$ and $R_2$ each may be the same as or different from each other; and $R_3$ and $R_4$ may be each independently (C1-C20)alkyl.

In order to obtain a more improved effect, $Y_1$ and $Y_2$ may be different from each other, and $Y_3$ and $Y_4$ may be different from each other, and more preferably, the organic semiconductor compound of the present disclosure may be represented by Chemical Formula 2 below:

[Chemical Formula 2]

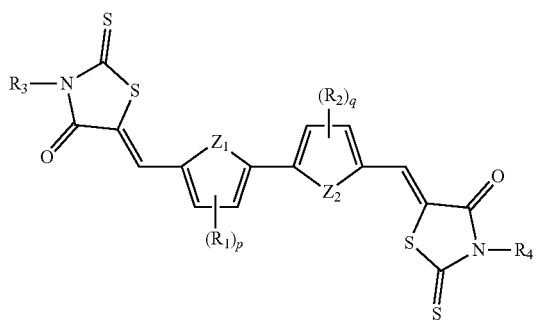

in Chemical Formula 2, $Z_1$ and $Z_2$ are each independently O, S, or Se;

$R_1$ and $R_2$ are each independently halogen, (C1-C20)alkyl, halo(C1-C20)alkyl or (C1-C20)alkoxycarbonyl;

p and q are each independently 0 or an integer of 1 to 2, and when p and q are 2, $R_1$ and $R_2$ each may be the same as or different from each other; and $R_3$ and $R_4$ are each independently (C1-C20)alkyl.

The organic semiconductor compound represented by Chemical Formula 2 has an absorption spectrum in a broader region by introducing a rhodanine functional group into the central backbone of two 5-membered heteroaromatic rings and has an excellent light absorption coefficient, and thus an organic electronic device obtained by employing the organic semiconductor compound has an extremely improved photoelectric conversion efficiency.

Preferably, in Chemical Formula 2 of the present disclosure, $Z_1$ and $Z_2$ may be equally O, S, or Se.

The organic semiconductor compound of the present disclosure may be selected from the following compounds, but is not limited thereto:

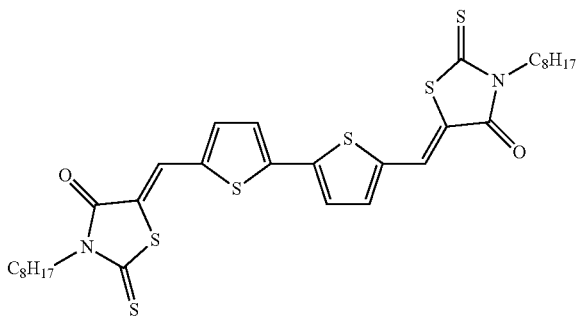

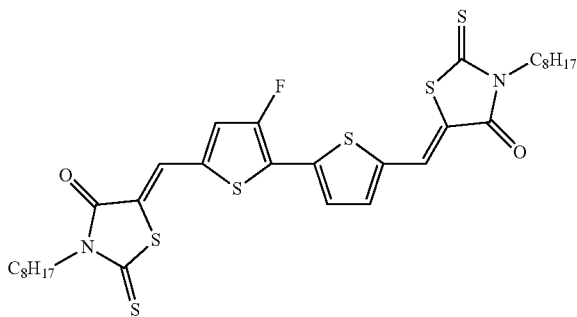

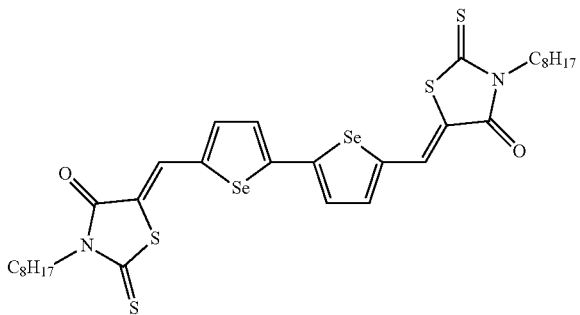

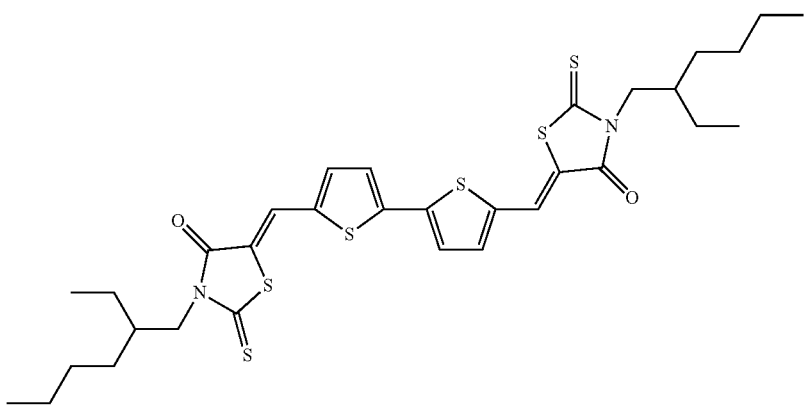

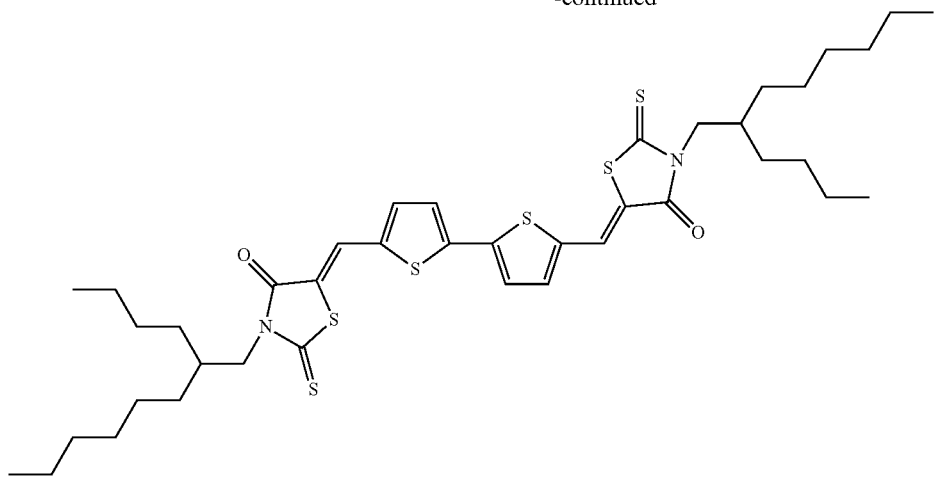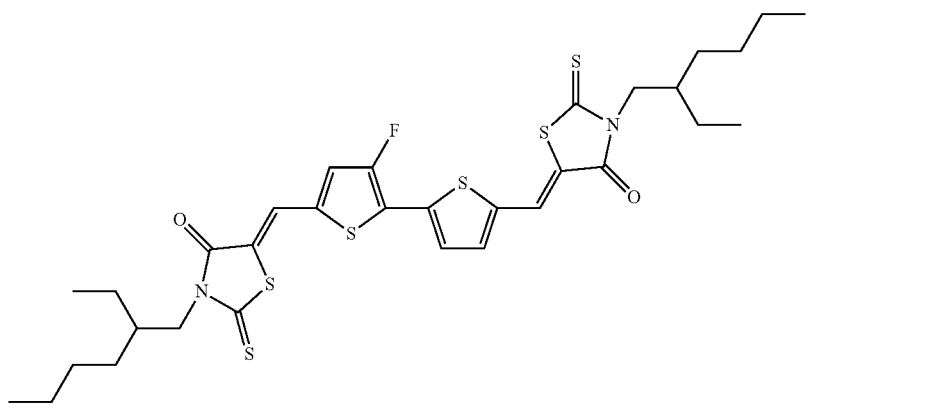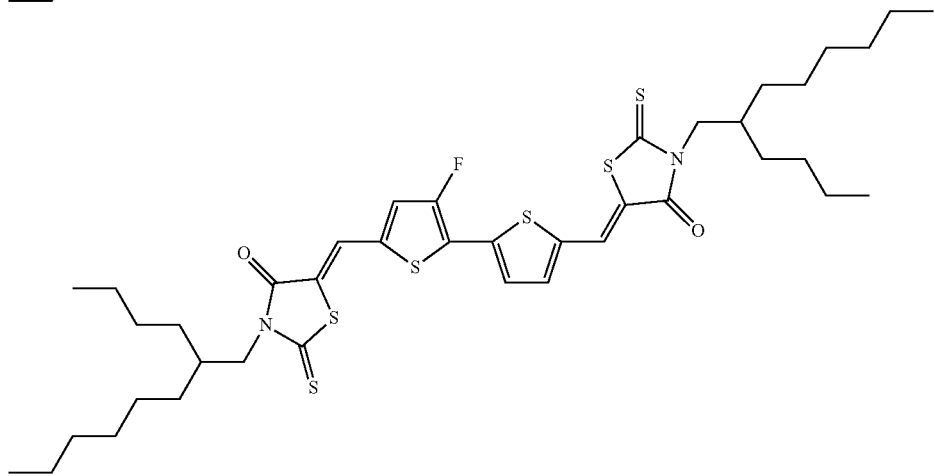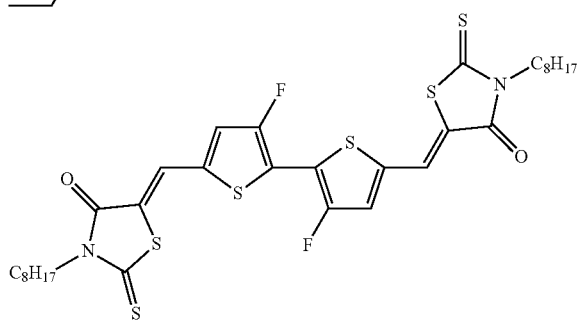

-continued
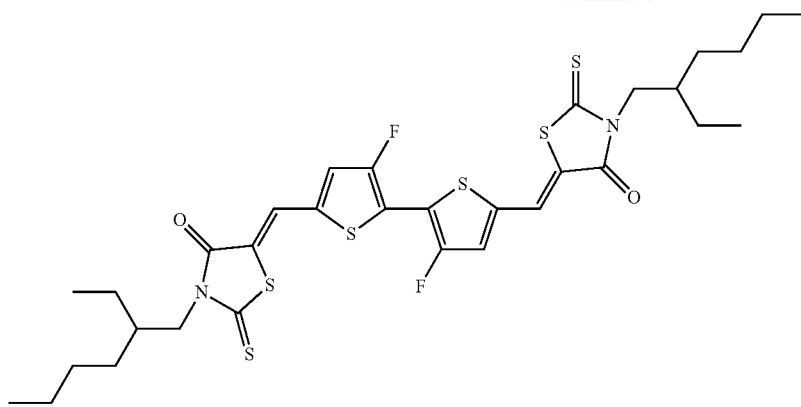
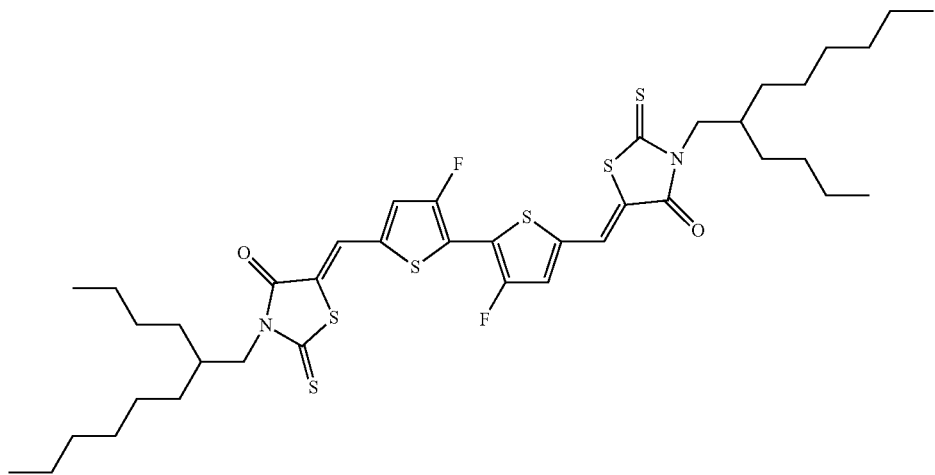 [SMILES: CCCCCCC(CCCC)CN1C(=O)/C(=C/c2cc(F)c(-c3sc(/C=C4\SC(=S)N(CC(CCCC)CCCCCC)C4=O)cc3F)s2)SC1=S]
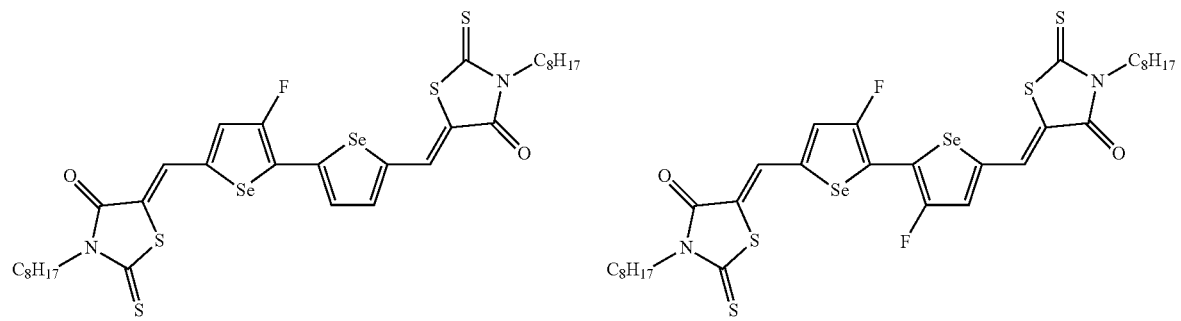
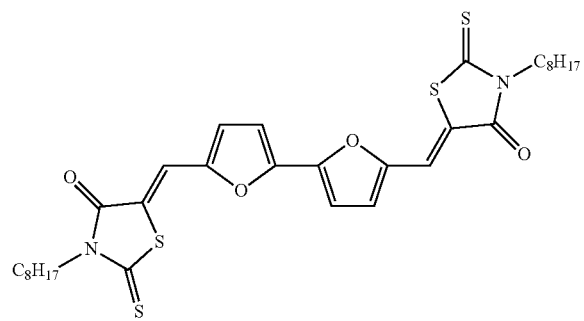

-continued
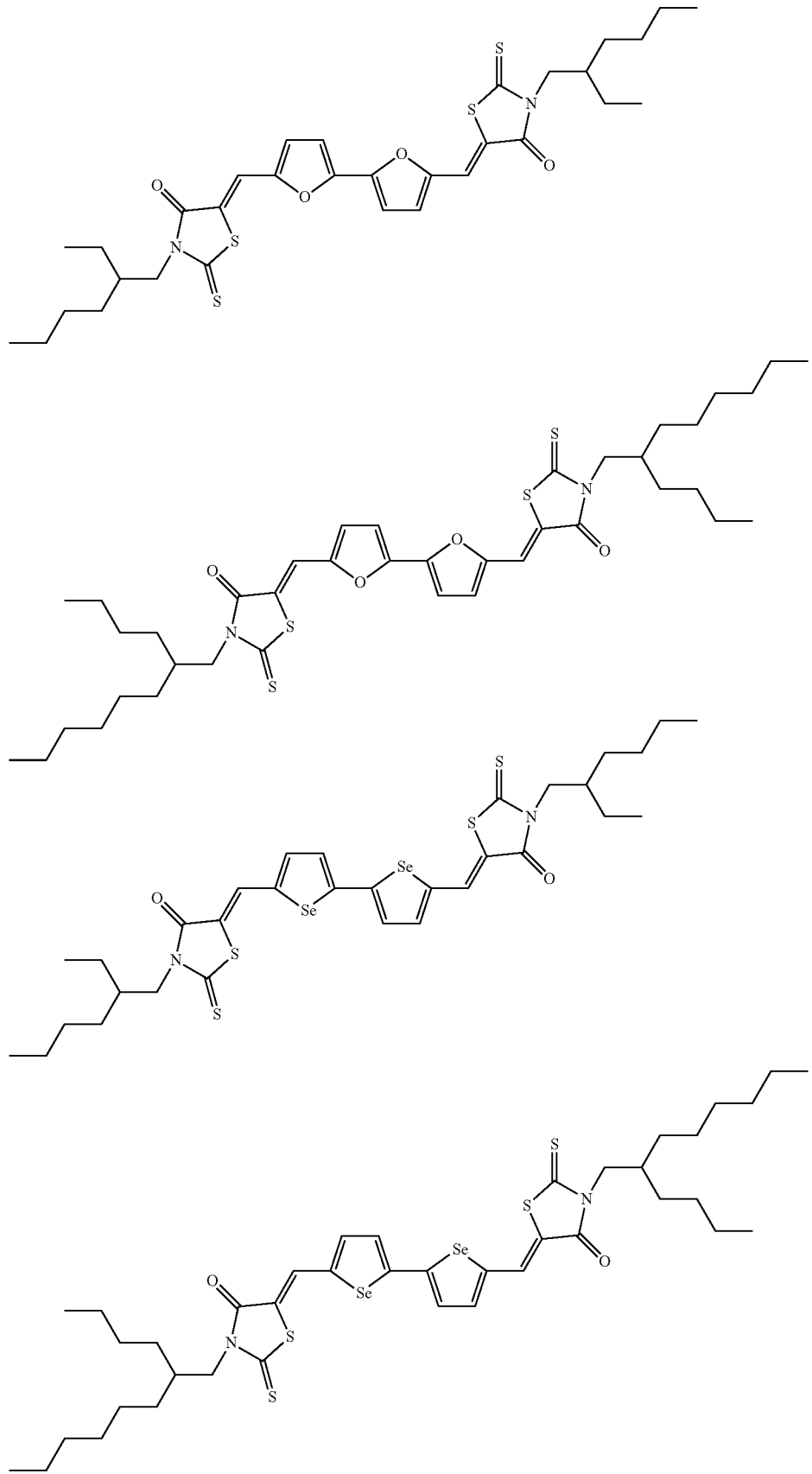

-continued
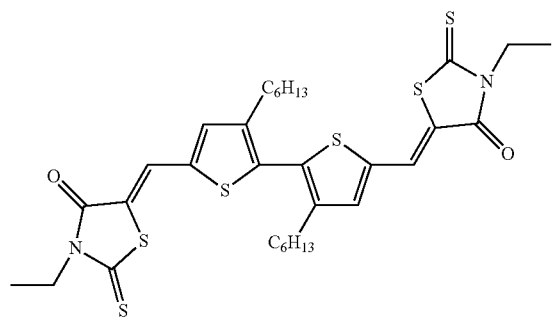
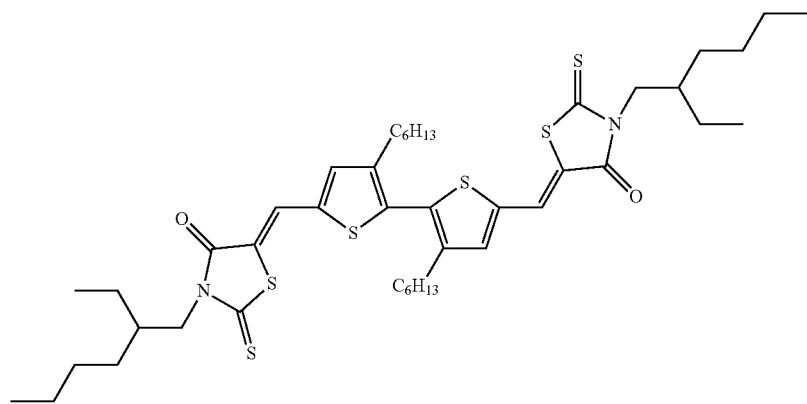
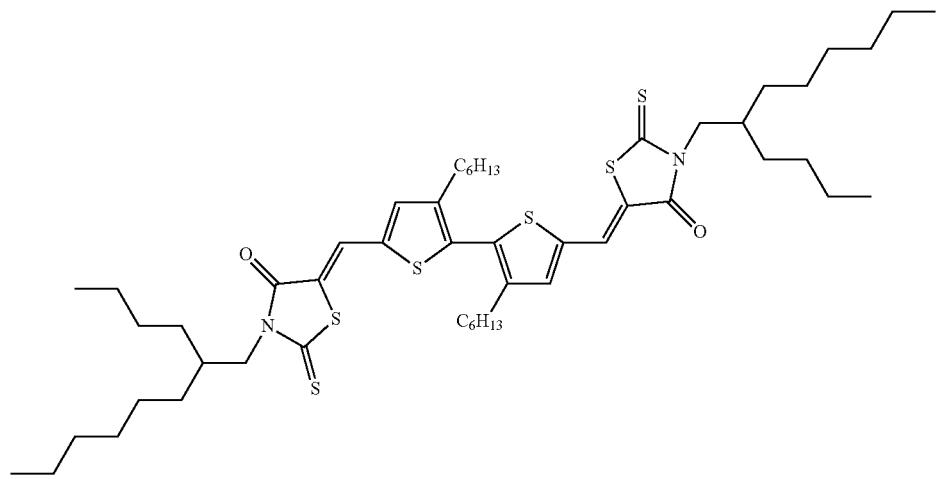
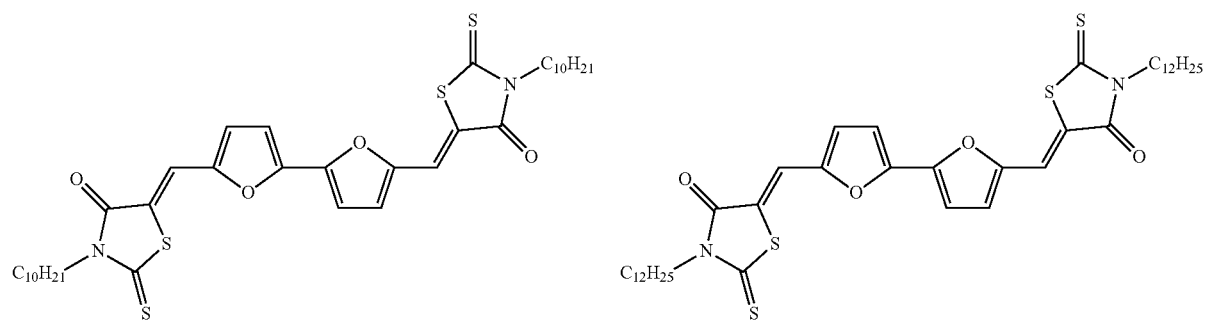

31 32
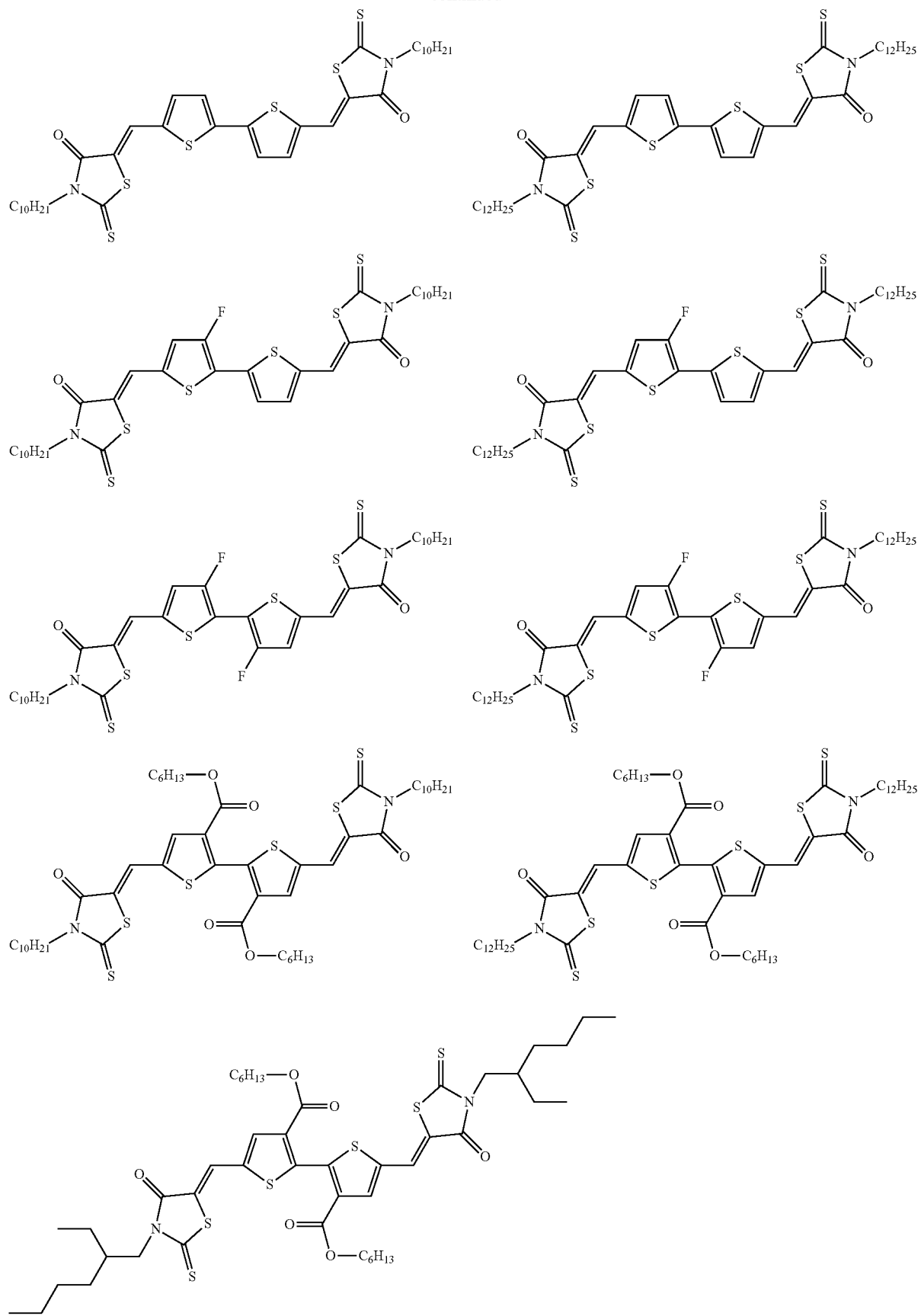
-continued

-continued
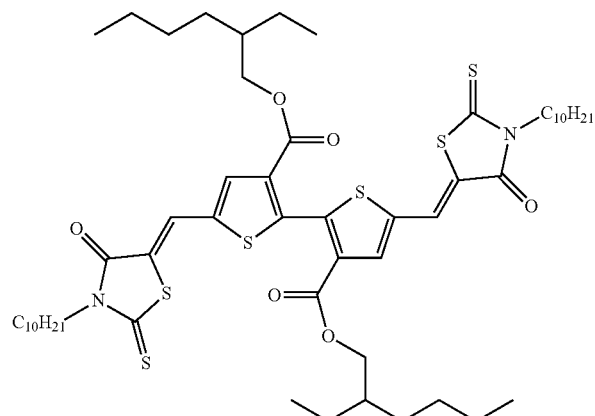
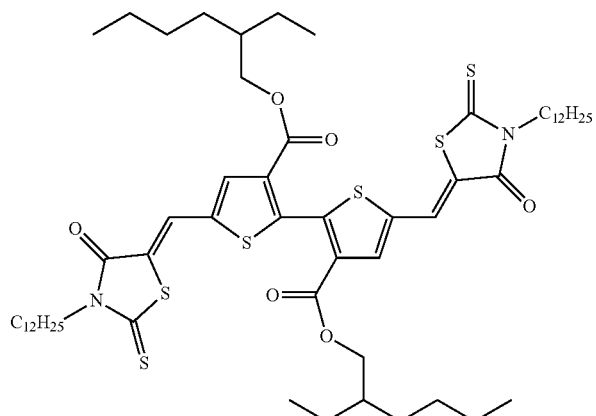
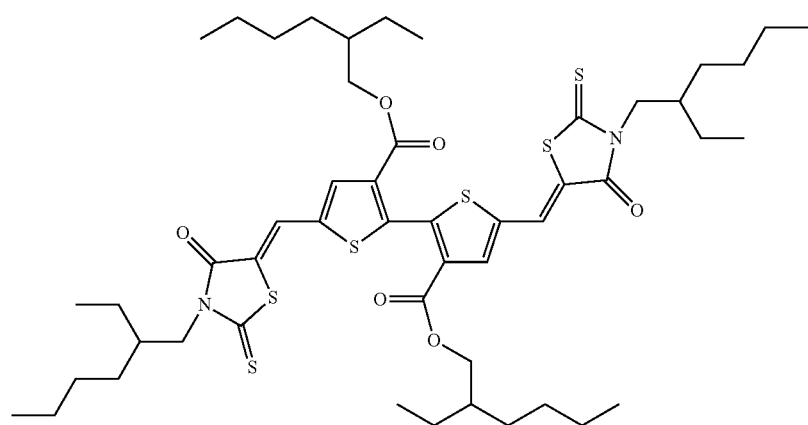
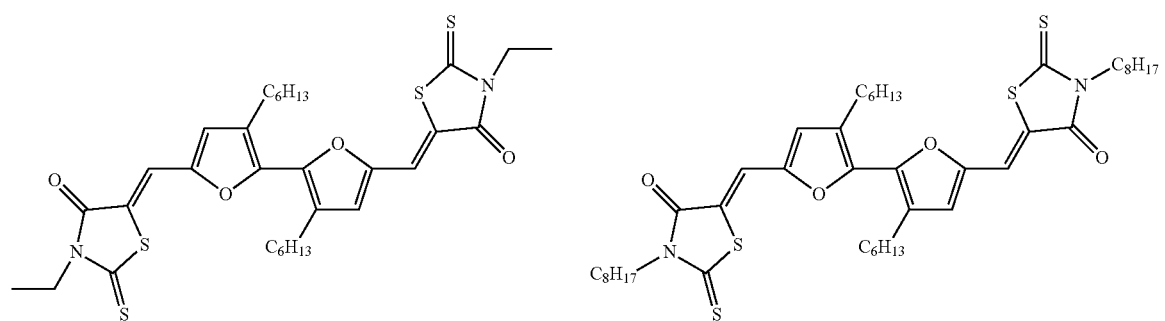
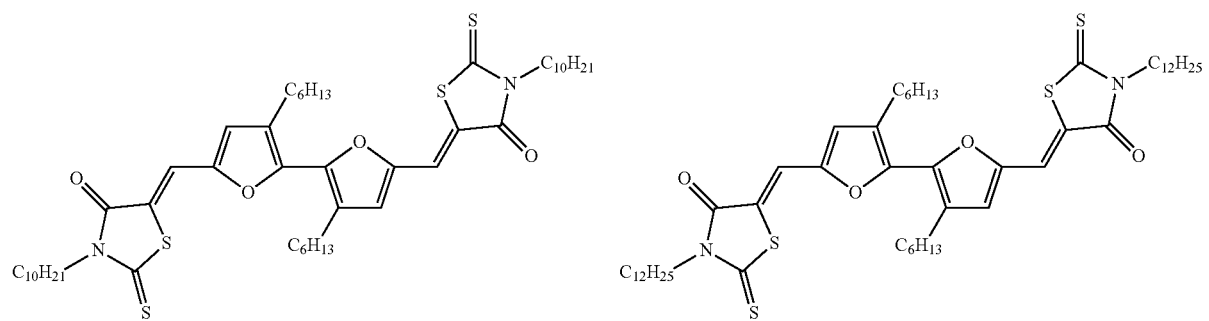

35 36
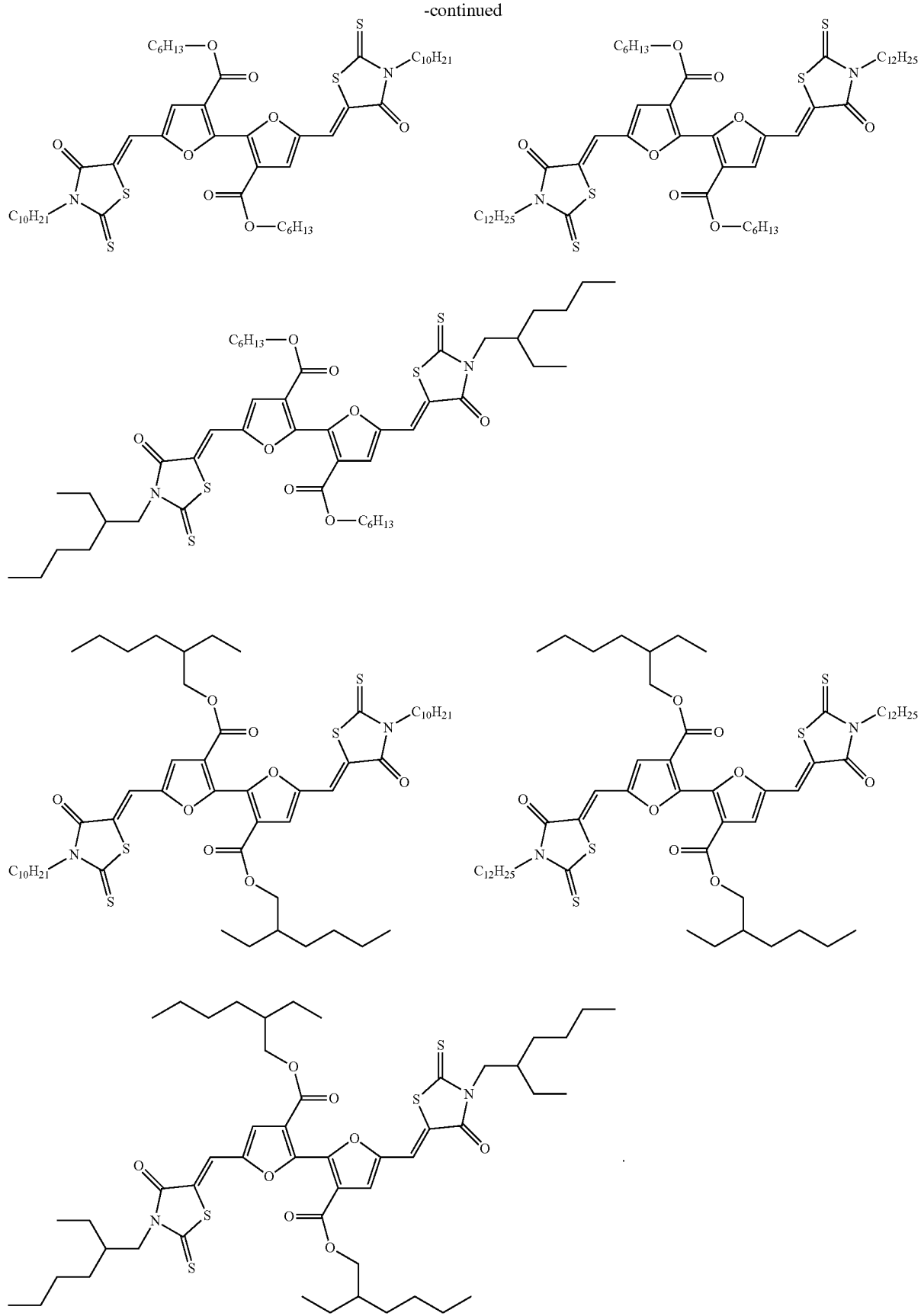
-continued

Terms 「alkyl」, 「alkoxy」, and other substituents including 「alkyl」 part described in the present disclosure include all linear or branched forms.

Term: 「aryl」 described in the present disclosure is an organic radical derived from aromatic hydrocarbon by removal of one hydrogen, and includes a single ring system or a fused ring system including 4 to 7 ring atoms, preferably, 5 or 6 ring atoms in each ring, and even includes a form in which a plurality of aryls are connected by a single bond.

Arylalkyl described in the present disclosure means a substituent in which at least one hydrogen present on the alkyl is substituted with aryl.

Haloalkyl means a substituent in which at least one hydrogen present on the alkyl is substituted with halogen.

Further, the '(C1-C20)alkyl' group described in the present disclosure is preferably (C1-C15)alkyl, and more preferably (C1-C10)alkyl. The '(C6-C20)aryl' group is preferably (C6-C18)aryl, and more preferably (C6-C12)aryl. '(C1-C20)alkoxy' group is preferably (C1-C15)alkoxy, and more preferably (C1-C10)alkoxy. '(C6-C20)aryl(C1-C20)alkyl' group is preferably (C6-C18)aryl(C1-C15)alkyl, and more preferably (C6-C12)aryl(C1-C10)alkyl.

The organic semiconductor compound represented by Chemical Formula 1 according to the present disclosure may be produced by including: reacting a dicarbaldehyde compound represented by Chemical Formula 3 below, a thiazolidine compound represented by Chemical Formula 4 below, and a thiazolidine compound represented by Chemical Formula 5 below to produce the organic semiconductor compound represented by Chemical Formula 1:

[Chemical Formula 3]

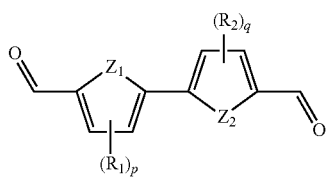

[Chemical Formula 4]

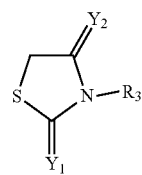

[Chemical Formula 5]

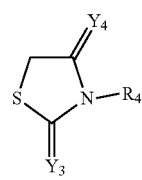

in Chemical Formulas 3 to 5, $Z_1$ and $Z_2$ are each independently O, S, or Se;

$Y_1$ to $Y_4$ are each independently O, S, Se or $CR^aR^b$, and $R^a$ and $R^b$ are each independently cyano, a carboxyl group, (C1-C20)alkyl, (C1-C20)alkoxy or (C1-C20)alkoxycarbonyl;

$R_1$ and $R_2$ are each independently halogen, (C1-C20)alkyl group, a halo(C1-C20)alkyl, (C1-C20)alkoxy, (C1-C20)alkylthio, (C1-C20)alkoxycarbonyl or (C6-C20)ar(C1-C20)alkyl;

p and q are each independently 0 or an integer of 1 to 2, and when p and q are 2, $R_1$ and $R_2$ each may be the same as or different from each other; and $R_3$ and $R_4$ are each independently hydrogen or (C1-C20)alkyl.

The organic semiconductor compound of the present disclosure is easy to be produced with a high purity and a high yield by a simple process to thereby have very high industrial applicability.

A solvent used in the production method of the present disclosure may be any conventional organic solvent, and may be preferably at least one selected from the group consisting of dichloromethane (DCM), dichloroethane (DCE), toluene, acetonitrile (MeCN), nitromethane, tetrahydrofuran (THF), N,N-dimethylformamide (DMF), and N,N-dimethylacetamide (DMA).

A reaction temperature is any temperature as long as it is a temperature used in general organic synthesis, but may vary according to a reaction time, a reaction material, and an amount of a starting material. After complete consumption of a starting material is confirmed by TLC, etc., the reaction is completed. When the reaction is completed, an extraction process is performed, then the solvent is distilled under reduced pressure, and a target material may be separated and purified by general methods such as column chromatography, and the like.

In addition, there is provided an organic electronic device including the organic semiconductor compound of the present disclosure.

The organic electronic device of the present disclosure may be any device as long as it is a device in which the organic semiconductor compound of the present disclosure is usable. For example, the organic electronic device may be an organic solar cell, an organic light emitting device, and an organic thin film transistor, and preferably, an organic solar cell. The organic semiconductor compound of the present disclosure may be included in a photoactive layer of the organic solar cell.

Preferably, the organic semiconductor compound of the present disclosure is an electron acceptor and is used as a compound for replacing a fullerene derivative that is conventionally used in the organic solar cell, and the organic solar cell in which the organic semiconductor compound is employed has improved photoelectric conversion efficiency.

Hereinafter, representative compounds of the present disclosure are described in detail through Examples and Comparative Examples for a detailed understanding of the present disclosure. Accordingly, the following Examples according to the present disclosure may be modified into various other forms, and the scope of the present disclosure should not be construed as being limited to Examples to be described below. These Examples of the present disclosure are provided to enable those skilled in the art to more fully understand the present disclosure.

[Example 1] Production of Small Molecular Organic Semiconductor Compound 1

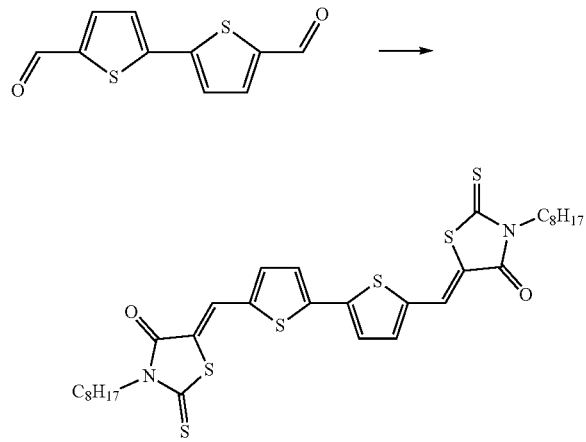

Piperidine (0.1 mL) was added to a chlorobenzene (5 mL) solution in which (2,2'-bithiophene)-5,5'-dicarbaldehyde (0.0111 g, 0.05 mmol) and 3-octylrhodanine (0.061 g, 0.25 mmol) were dissolved, refluxed under argon atmosphere for 13 hours, and cooled to room temperature. When a reaction solution was dropped into methanol (20 mL), a precipitate was formed, the resulting precipitate was filtered, and dissolved again with a minimum amount of chloroform, and then precipitated again with methanol. The obtained product was separated by column chromatography, thereby obtaining an organic semiconductor compound 1.

$^1$H-NMR (300 MHz, CDCl$_3$): δ 7.82 (s, 2H), 7.38 (d, 2H), 7.35 (d, 2H) 4.11 (t, 4H) 1.71 (m, 4H) 1.30 (m, 20H), 0.88 (t, 6H).

[Example 2] Production of Small Molecular Organic Semiconductor Compound 2

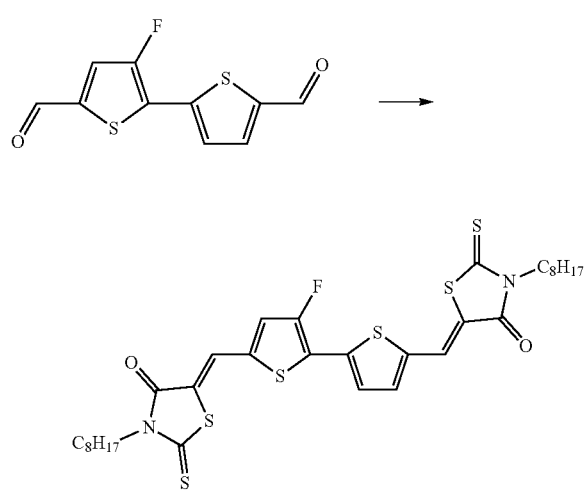

Piperidine (0.1 mL) was added to a chlorobenzene (5 mL) solution in which 3-fluoro-(2,2'-bithiophene)-5,5'-dicarbaldehyde (0.012 g, 0.05 mmol) and 3-octylrhodanine (0.061 g, 0.25 mmol) were dissolved, refluxed under argon atmosphere for 13 hours, and cooled to room temperature. When a reaction solution was dropped into methanol (20 mL), a precipitate was formed, the resulting precipitate was filtered, and dissolved again with a minimum amount of chloroform, and then precipitated again with methanol. The obtained product was separated by column chromatography, thereby obtaining an organic semiconductor compound 2.

$^1$H-NMR (300 MHz, CDCl$_3$): δ 7.84 (s, 1H), 7.69 (s, 1H), 7.42 (s, 1H), 7.39 (s, 1H), 7.38 (s, 1H), 7.26 (s, 1H), 4.11 (t, 4H) 1.71 (m, 4H) 1.34 (m, 20H), 0.88 (t, 6H).

[Example 3] Production of Small Molecular Organic Semiconductor Compound 3

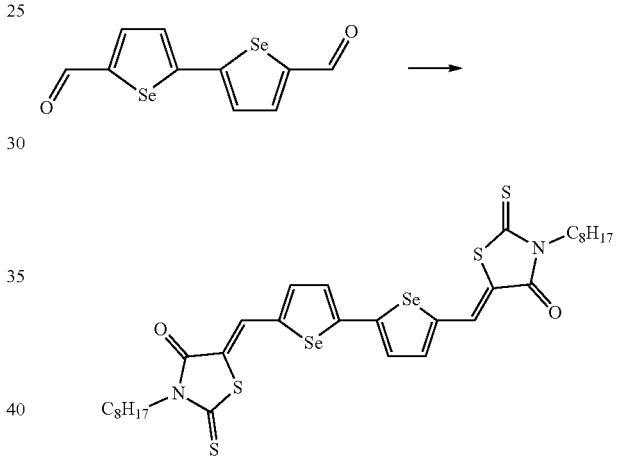

Piperidine (0.1 mL) was added to a chlorobenzene (5 mL) solution in which (2,2'-biselenophene)-5,5'-dicarbaldehyde (0.015 g, 0.05 mmol) and 3-octylrhodanine (0.061 g, 0.25 mmol) were dissolved, refluxed under argon atmosphere for 13 hours, and cooled to room temperature. When a reaction solution was dropped into methanol (20 mL), a precipitate was formed, the resulting precipitate was filtered, and dissolved again with a minimum amount of chloroform, and then precipitated again with methanol. The obtained product was separated by column chromatography, thereby obtaining an organic semiconductor compound 3.

$^1$H-NMR (300 MHz, CDCl$_3$): δ 7.82 (s, 2H), 7.35 (d, 2H), 7.32 (d, 2H) 4.11 (t, 4H) 1.71 (m, 4H) 1.30 (m, 20H), 0.88 (t, 6H)

[Examples 4 to 44]

Organic semiconductor compounds 4 to 44 were produced by using the production methods of Examples 1 to 3, and structures and 1H NMR of the produced organic semiconductor compounds are shown in Table 1 below.

TABLE 1
| Example | Structure of organic semiconductor compound | $^1$H NMR [300 MHz, CDCl$_3$] |
|---|---|---|
| 4 | 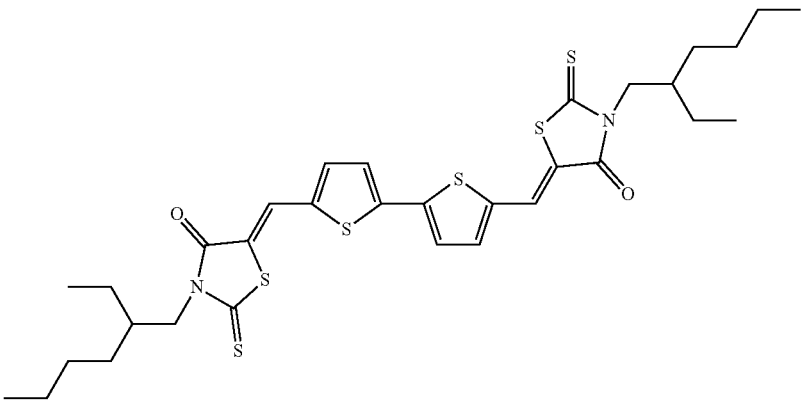 | δ 7.89 (d, 2H), 7.86 (d, 2H), 7.42 (s, 2H), 4.11 (d, 4H), 1.92 (m, 2H), 1.55 (m, 4H), 1.31-1.25 (m, 8H), 1.19 (m, 4H), 0.88 (t, 12H) |
| 5 | 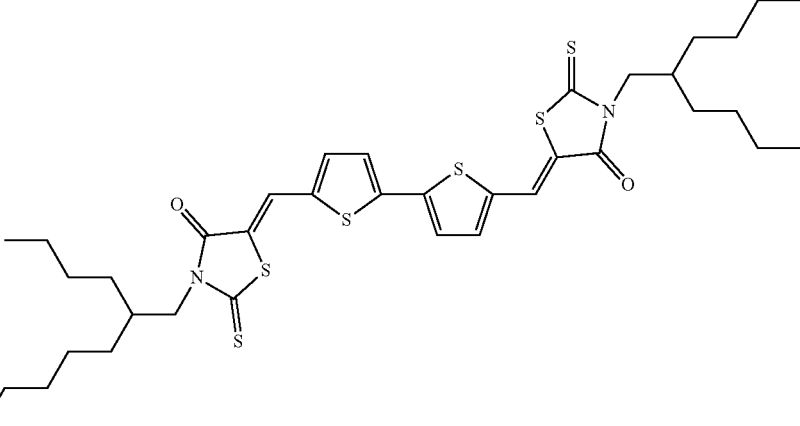 | δ 7.89 (d, 2H), 7.86 (d, 2H), 7.42 (s, 2H), 4.11 (d, 4H), 1.92 (m, 2H), 1.31-1.25 (m, 32H), 0.88 (t, 12H) |
| 6 | 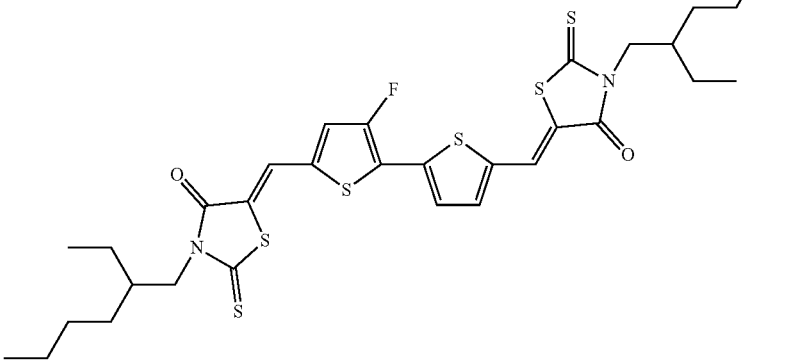 | δ 7.89 (d, 1H), 7.86 (d, 1H), 7.43 (d, 1H), 7.42 (s, 2H), 4.11 (d, 4H), 1.92 (m, 2H), 1.55 (m, 4H), 1.31-1.19 (m, 12H), 0.88 (t, 12H) |

TABLE 1-continued

| Example | Structure of organic semiconductor compound | $^1$H NMR [300 MHz, CDCl$_3$] |
|---|---|---|
| 7 | | δ 7.89 (d, 1H), 7.86 (d, 1H), 7.43 (d, 1H), 7.42 (s, 2H), 4.11 (d, 4H), 1.92 (m, 2H), 1.31-1.19 (m, 32H), 0.88 (t, 12H) |
| 8 | | δ 7.43 (s, 2H), 7.42 (s, 2H), 4.03 (d, 4H), 1.63 (m, 2H), 1.28-1.26 (m, 20H), 0.88 (t, 6H) |
| 9 | | δ 7.43 (s, 2H), 7.42 (s, 2H), 4.03 (d, 4H), 1.92 (m, 2H), 1.55 (m, 2H), 1.31-1.19 (m, 12H), 0.88 (t, 12H) |

TABLE 1-continued
| Example | Structure of organic semiconductor compound | $^1$H NMR [300 MHz, CDCl$_3$] |
|---|---|---|
| 10 | 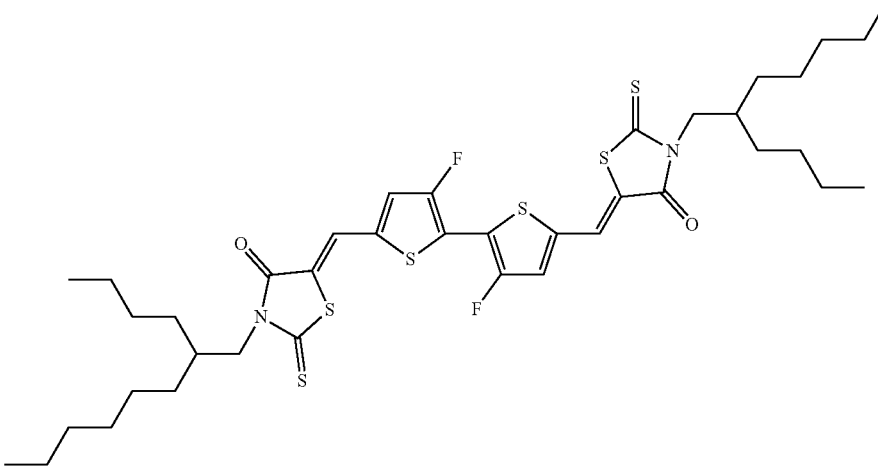 | δ 7.43 (s, 2H), 7.42 (s, 2H), 4.03 (d, 4H), 1.92 (m, 2H), 1.31-1.19 (m, 28H), 0.88 (t, 12H) |
| 11 | 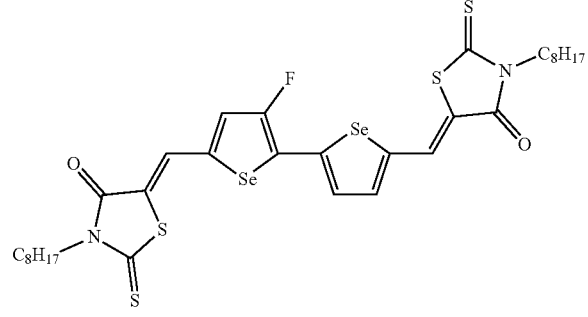 | δ 7.28 (s, 2H), 7.14 (s, 3H), 4.03 (d, 4H), 1.63 (m, 4H), 1.28-1.26 (m, 20H), 0.88 (t, 6H) |
| 12 | 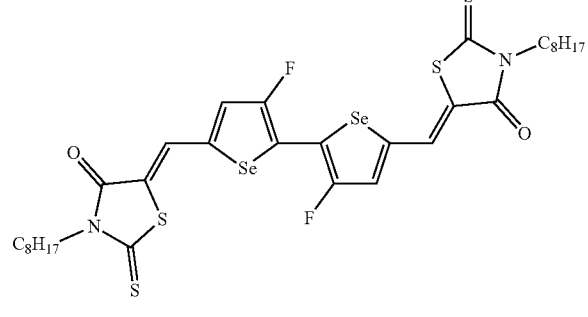 | δ 7.28 (s, 2H), 7.14 (s, 2H), 4.03 (d, 4H), 1.63 (m, 4H), 1.28-1.26 (m, 20H), 0.88 (t, 6H) |
| 13 | 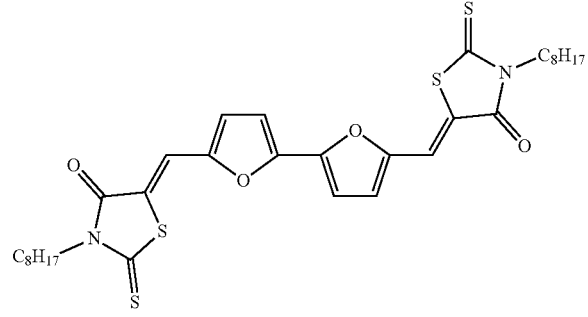 | δ 7.52 (d, 2H), 7.42 (d, 2H), 7.37 (s, 2H), 4.03 (d, 4H), 1.63 (m, 4H), 1.28-1.26 (m, 20H), 0.88 (t, 6H) |

TABLE 1-continued
| Example | Structure of organic semiconductor compound | $^1$H NMR [300 MHz, CDCl$_3$] |
|---|---|---|
| 14 | 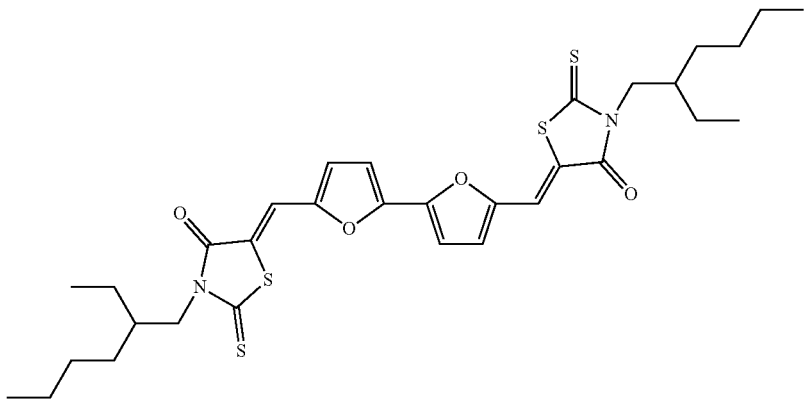 | δ 7.52 (d, 2H), 7.42 (d, 2H), 7.37 (s, 2H), 4.11 (d, 4H), 1.92 (m, 2H), 1.55 (m, 4H), 1.31-1.19 (m, 12H), 0.88 (t, 12H) |
| 15 | 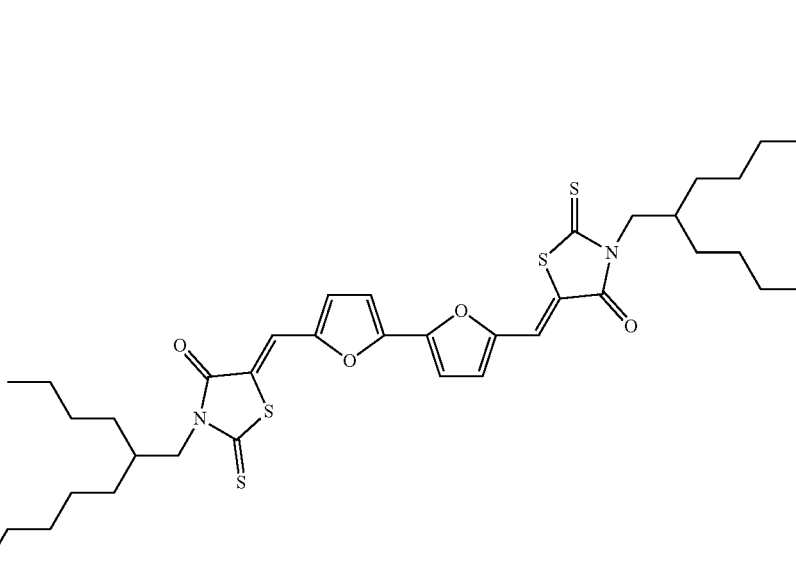 | δ 7.52 (d, 2H), 7.42 (d, 2H), 7.37 (s, 2H), 4.11 (d, 4H), 1.92 (m, 2H), 1.31-1.19 (m, 32H), 0.88 (t, 12H) |
| 16 | 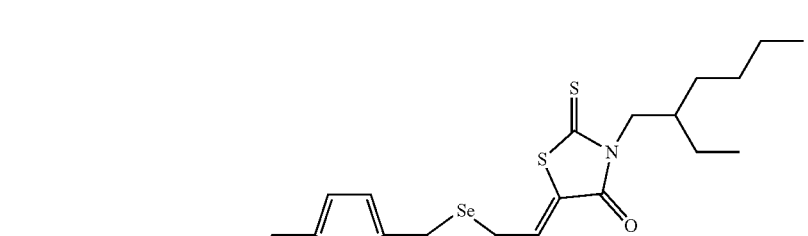 | δ 7.28 (s, 2H), 7.14 (s, 4H), 4.11 (d, 4H), 1.92 (m, 2H), 1.55 (m, 4H), 1.31-1.19 (m, 12H), 0.88 (t, 12H) |

TABLE 1-continued

| Example | Structure of organic semiconductor compound | $^1$H NMR [300 MHz, CDCl$_3$] |
| --- | --- | --- |
| 17 | | δ 7.28 (d, 2H), 7.14 (s, 4H), 4.11 (d, 4H), 1.92 (m, 2H), 1.31-1.19 (m, 32H), 0.88 (t, 12H) |
| 18 | | δ 7.56 (s, 2H), 7.42 (s, 2H), 4.07 (q, 4H), 2.68 (t, 4H), 1.50 (m, 4H), 1.30-1.20 (m, 18H), 0.88 (t, 6H) |
| 19 | | δ 7.56 (s, 2H), 7.42 (s, 2H), 4.11 (d, 4H), 2.68 (t, 4H), 1.92 (m, 2H), 1.55-1.50 (m, 8H), 1.31-1.19 (m, 24H), 0.88 (t, 18H) |

TABLE 1-continued

| Example | Structure of organic semiconductor compound | $^1$H NMR [300 MHz, CDCl$_3$] |
|---|---|---|
| 20 | | δ 7.56 (s, 2H), 7.42 (s, 2H), 4.11 (d, 4H), 2.68 (t, 4H), 1.92 (m, 2H), 1.50 (m, 4H), 1.31-1.19 (m, 44H), 0.88 (t, 18H) |
| 21 | | δ 7.52 (d, 2H), 7.42 (d, 2H), 7.37 (s, 2H), 4.03 (t, 4H), 1.63 (m, 4H), 1.28-1.26 (m, 28H), 0.88 (t, 6H) |
| 22 | | [300 MHz, CHCl$_3$]: δ 7.52 (d, 2H), 7.42 (d, 2H), 7.37 (s, 2H), 4.03 (t, 4H), 1.63 (m, 4H), 1.28-1.26 (m, 36H), 0.88 (t, 6H) |
| 23 | | δ 7.89-7.86 (m, 4H), 7.42 (s, 2H), 4.03 (t, 4H), 1.63 (m, 4H), 1.28-1.26 (m, 28H), 0.88 (t, 6H) |

TABLE 1-continued

| Example | Structure of organic semiconductor compound | ¹H NMR [300 MHz, CDCl₃] |
|---|---|---|
| 24 | | δ 7.89-7.86 (m, 4H), 7.42 (s, 2H), 4.03 (t, 4H), 1.63 (m, 4H), 1.28-1.26 (m, 36H), 0.88 (t, 6H) |
| 25 | | δ 7.89-7.86 (m, 2H), 7.43 (d, 1H), 7.42 (s, 2H), 4.03 (t, 4H), 1.63 (m, 4H), 1.28-1.26 (m, 28H), 0.88 (t, 6H) |
| 26 | | δ 7.89-7.86 (m, 2H), 7.43 (d, 1H), 7.42 (s, 2H), 4.03 (t, 4H), 1.63 (m, 4H), 1.28-1.26 (m, 36H), 0.88 (t, 6H) |
| 27 | | δ 7.43 (s, 2H), 7.42 (s, 2H), 4.03 (t, 4H), 1.63 (m, 4H), 1.28-1.26 (m, 28H), 0.88 (t, 6H) |

TABLE 1-continued

| Example | Structure of organic semiconductor compound | ¹H NMR [300 MHz, CDCl₃] |
|---|---|---|
| 28 | | δ 7.43 (s, 2H), 7.42 (s, 2H), 4.03 (t, 4H), 1.63 (m, 4H), 1.28-1.26 (m, 36H), 0.88 (t, 6H) |
| 29 | | δ 8.10 (s, 2H), 7.42 (s, 2H), 4.33 (t, 4H), 4.03 (t, 4H), 1.78 (m, 4H), 1.63 (m, 4H), 1.39-1.37 (m, 12H), 1.28-1.26 (m, 28H), 0.88 (t, 12H) |
| 30 | | δ 8.10 (s, 2H), 7.42 (s, 2H), 4.33 (t, 4H), 4.03 (t, 4H), 1.78 (m, 4H), 1.63 (m, 4H), 1.39-1.37 (m, 12H), 1.28-1.26 (m, 36H), 0.88 (t, 12H) |
| 31 | | δ 8.10 (s, 2H), 7.42 (s, 2H), 4.33 (t, 4H), 4.11 (t, 4H), 1.92 (m, 2H), 1.78 (m, 4H), 1.55 (m, 4H), 1.39-1.37 (m, 12H), 1.31-1.25 (m, 12H), 0.88 (t, 18H) |

TABLE 1-continued
| Example | Structure of organic semiconductor compound | $^1$H NMR [300 MHz, CDCl$_3$] |
|---|---|---|
| 32 | 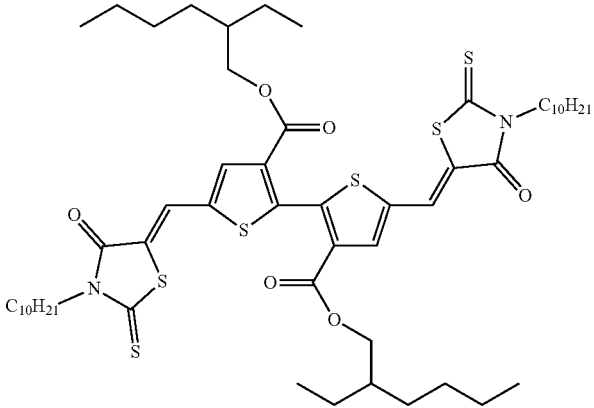 | δ 8.10 (s, 2H), 7.42 (s, 2H), 4.33 (t, 4H), 4.11 (t, 4H), 1.92 (m, 2H), 1.78 (m, 4H), 1.55 (m, 4H), 1.39-1.37 (m, 12H), 1.31-1.25 (m, 12H), 0.88 (t, 18H) |
| 33 | 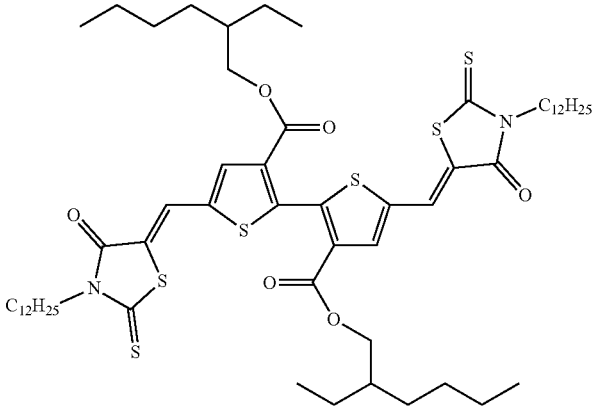 | δ 8.10 (s, 2H), 7.42 (s, 2H), 4.66 (d, 4H), 4.03 (t, 4H), 1.89 (m, 2H), 1.63 (m, 4H), 1.55 (m, 4H), 1.31-1.25 (m, 44H), 0.88 (t, 18H) |
| 34 | 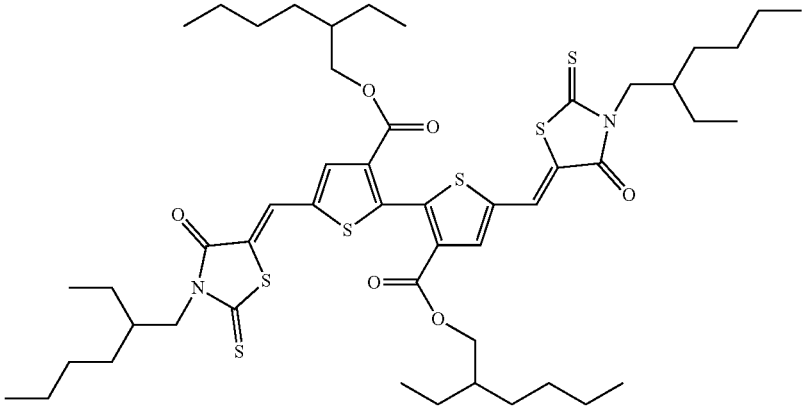 | δ 8.10 (s, 2H), 7.42 (s, 2H), 4.66 (d, 4H), 4.11 (t, 4H), 1.92-1.89 (m, 4H), 1.55 (m, 8H), 1.31-1.19 (m, 24H), 0.88 (t, 24H) |
| 35 | 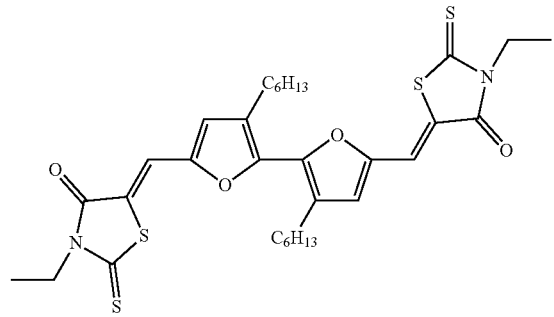 | δ 7.37 (s, 2H), 6.94 (s, 2H), 4.07 (q, 4H), 2.63 (t, 4H), 1.59 (m, 4H), 1.30-1.29 (m, 12H), 1.20 (t, 6H), 0.88 (t, 6H) |

TABLE 1-continued

| Example | Structure of organic semiconductor compound | $^1$H NMR [300 MHz, CDCl$_3$] |
|---|---|---|
| 36 | | δ 7.37 (s, 2H), 6.94 (s, 2H), 4.03 (t, 4H), 2.63 (t, 4H), 1.63-1.59 (m, 8H), 1.30-1.26 (m, 32H), 0.88 (t, 12H) |
| 37 | | δ 7.37 (s, 2H), 6.94 (s, 2H), 4.03 (t, 4H), 2.63 (t, 4H), 1.63-1.59 (m, 8H), 1.30-1.26 (m, 40H), 0.88 (t, 12H) |
| 38 | | δ 7.37 (s, 2H), 6.94 (s, 2H), 4.03 (t, 4H), 2.63 (t, 4H), 1.63-1.59 (m, 8H), 1.30-1.26 (m, 48H), 0.88 (t, 12H) |
| 39 | | δ 7.59 (s, 2H), 7.37 (s, 2H), 4.33 (t, 4H), 4.03 (t, 4H), 1.78 (m, 4H), 1.63 (m, 4H), 1.39-1.26 (m, 40H), 0.88 (t, 12H) |

TABLE 1-continued

| Example | Structure of organic semiconductor compound | ¹H NMR [300 MHz, CDCl₃] |
|---|---|---|
| 40 | | δ 7.59 (s, 2H), 7.37 (s, 2H), 4.33 (t, 4H), 4.03 (t, 4H), 1.78 (m, 4H), 1.63 (m, 4H), 1.39-1.26 (m, 48H), 0.88 (t, 12H) |
| 41 | | δ 7.59 (s, 2H), 7.37 (s, 2H), 4.33 (t, 4H), 4.11 (t, 4H), 1.92 (m, 2H), 1.78 (m, 4H), 1.55 (m, 4H), 1.39-1.19 (m, 24H), 0.88 (t, 18H) |
| 42 | | δ 7.59 (s, 2H), 7.37 (s, 2H), 4.66 (t, 4H), 4.03 (t, 4H), 1.89 (m, 2H), 1.63 (m, 4H), 1.55 (m, 4H), 1.39-1.19 (m, 40H), 0.88 (t, 18H) |
| 43 | | δ 7.59 (s, 2H), 7.37 (s, 2H), 4.66 (t, 4H), 4.03 (t, 4H), 1.89 (m, 2H), 1.63 (m, 4H), 1.55 (m, 4H), 1.31-1.19 (m, 48H), 0.88 (t, 18H) |

TABLE 1-continued

| Example | Structure of organic semiconductor compound | $^1$H NMR [300 MHz, CDCl$_3$] |
|---|---|---|
| 44 | | δ 7.59 (s, 2H), 7.37 (s, 2H), 4.66 (d, 4H), 4.11 (t, 4H), 1.92-1.89 (m, 4H), 1.55 (m, 8H), 1.31-1.19 (m, 24H), 0.88 (t, 24H) |

[Examples 45 to 64] Production of Organic Solar Cell Including Small Molecular Organic Semiconductor Compound An organic substrate coated with indium tin oxide (ITO), which is a positive electrode transparent electrode (first electrode), was immersed in deionized water including a washing solution, washed in an ultrasonic cleaner for 15 minutes, and washed again with deionized water, acetone and IPA three times, and then dried in an oven at 130 for 5 hours. The cleaned ITO glass substrate was subjected to ultraviolet/ozone treatment for 15 minutes, and ZnO.NPs having a thickness of 30 nm was spin-coated on the ITO substrate. Further, the substrate coated with ZnO.NPs was heat treated on a hot plate at 100 for 10 minutes. In addition, in order to coat a photoactive layer, the device was then transferred to a glove box filled with argon. The photoactive layer was produced by applying an organic semiconductor solution on the ZnO layer at a thickness of 100 nm by a spin coating method, the organic semiconductor solution being obtained by dissolving the organic semiconductor compound of the present disclosure described in Table 2 below and PTB7-TH(Poly[4,8-bis(5-(2-ethylhexyl)thiophen-2-yl)benzo[1,2-b;4,5-b']dithiophene-2,6-diyl-alt-(4-(2-ethylhexyl)-3-fluorothieno[3,4-b]thiophene-)-2-carboxylate-2-6-diyl)]) donor polymer in a chloroform solvent at a weight ratio of 1:1, followed by filtering using a 0.45 μm (PTFE) syringe filter. On the photoactive layer of the obtained device structure, MoO$_3$ having a thickness of 10 nm was deposited, and a 100 nm thick Ag electrode as a top electrode was deposited under 3×10$^{-6}$ torr vacuum in a thermal evaporator to complete an organic solar cell.

Open cell voltage (Voc), short circuit current (Jsc), fill factor (FF) and power conversion efficiency (PCE) which are electrical characteristics of the produced organic solar cell are shown in Table 2 below.

[Comparative Examples 1 and 2] Production of Organic Solar Cell

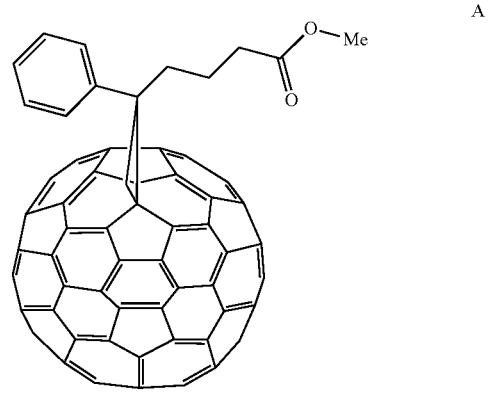

A

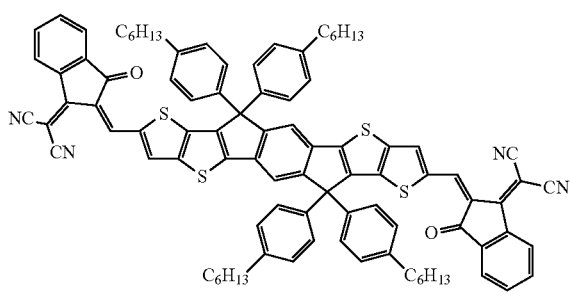

ITIC

An organic solar cell was produced by the same method as Example 45 except that the fullerene compound A having the above structure (Comparative Example 1) and a conventionally known non-fullerene-based compound ITIC (Comparative Example 2) were used instead of the organic semiconductor compound of the present disclosure, and electrical characteristics thereof are shown in Table 2 below.

TABLE 2

| Organic solar cell | Electron acceptor | Voc [V] | Jsc [mA/cm$^2$] | FF [%] | PCE [%] |
|---|---|---|---|---|---|
| Example 45 | Example 1 | 1.05 | 14.70 | 59 | 9.02 |
| Example 46 | Example 2 | 1.07 | 13.20 | 59 | 8.33 |
| Example 47 | Example 3 | 1.01 | 15.10 | 57 | 8.69 |
| Example 48 | Example 4 | 1.00 | 14.50 | 58 | 8.41 |
| Example 49 | Example 5 | 1.00 | 14.30 | 57 | 8.15 |
| Example 50 | Example 6 | 1.02 | 14.54 | 58 | 8.60 |
| Example 51 | Example 7 | 1.01 | 14.21 | 57 | 8.18 |
| Example 52 | Example 9 | 1.01 | 14.20 | 57 | 8.17 |
| Example 53 | Example 11 | 1.02 | 14.80 | 58 | 8.76 |
| Example 54 | Example 12 | 1.03 | 14.60 | 57 | 8.57 |
| Example 55 | Example 13 | 1.04 | 14.20 | 56 | 8.27 |
| Example 56 | Example 14 | 1.02 | 14.00 | 56 | 8.00 |
| Example 57 | Example 16 | 0.99 | 14.80 | 58 | 8.50 |
| Example 58 | Example 17 | 1.00 | 14.70 | 57 | 8.38 |
| Example 59 | Example 18 | 1.03 | 14.10 | 57 | 8.28 |
| Example 60 | Example 21 | 1.04 | 14.07 | 55 | 8.05 |
| Example 61 | Example 23 | 1.02 | 14.10 | 57 | 8.03 |
| Example 62 | Example 24 | 1.02 | 14.07 | 56 | 8.04 |
| Example 63 | Example 25 | 1.05 | 14.23 | 57 | 8.52 |
| Example 64 | Example 26 | 1.04 | 14.19 | 56 | 8.26 |
| Comparative Example 1 | Fullerene compound A | 0.80 | 16.13 | 57 | 7.35 |
| Comparative Example 2 | ITIC | 0.82 | 14.08 | 65 | 7.46 |

As shown in Table 2, it may be appreciated that the organic semiconductor compound of the present disclosure in which the rhodanine functional group is introduced into the central backbone of two 5-membered heteroaromatic rings may be used as a compound for replacing a conventional fullerene derivative to thereby have high electron affinity while simultaneously having excellent miscibility with the electron acceptor, thereby having high photoelectric conversion efficiency.

In addition, it may be appreciated that the organic semiconductor compound of the present disclosure may have the electron affinity higher than that of the conventionally known non-fullerene-based compound ITIC, and simultaneously, may also be excellent in miscibility with the electron donor, and thus the organic semiconductor compound may have a high photoelectric conversion efficiency.

The organic semiconductor compound of the present disclosure has high light absorption and absorption spectrum in almost all wavelength (panchromatic) regions in a visible light region to thereby be usable as various organic semiconductor compounds and to be very useful as a photoelectric conversion material.

Further, the novel organic semiconductor compound of the present disclosure has a low lowest unoccupied molecular orbital energy level (LUMO) to be usable as an electron acceptor, thereby being very useful as a photoelectric conversion material.

Further, the novel organic semiconductor compound of the present disclosure may have high crystallinity to have high charge mobility, and thus the organic electronic device including the organic semiconductor compound may have high efficiency.

In addition, the novel organic semiconductor compound of the present disclosure is a small molecule and may be produced with a high purity and a high yield by a simple process to thereby have very high industrial applicability. In particular, the organic semiconductor compound of the present disclosure is used as the compound for replacing the fullerene derivative in an organic solar cell device using fullerene the electron acceptor according to the related art, thereby remarkably improving stability and efficiency of the organic solar cell to have very high utilization possibility as a non-fullerene-based electron acceptor.

What is claimed is:

1. An organic semiconductor compound represented by Chemical Formula 1 below:

[Chemical Formula 1]

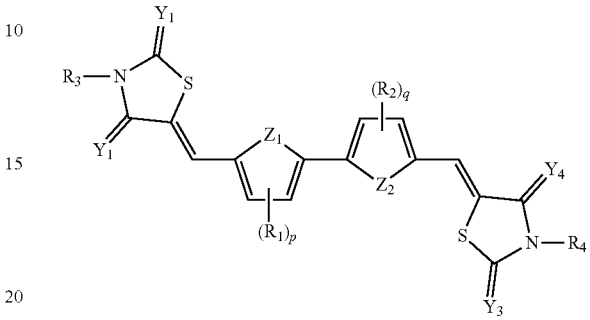

in Chemical Formula 1, $Z_1$ and $Z_2$ are each independently O, S, or Se;

$Y_1$ to $Y_4$ are each independently O, S, Se or $CR^aR^b$, and $R^a$ and $R^b$ are each independently cyano, a carboxyl group, (C1-C20) alkyl, (C1-C20) alkoxy or (C1-C20) alkoxycarbonyl;

$R_1$ and $R_2$ are each independently halogen, (C1-C20) alkyl, halo (C1-C20) alkyl, (C1-C20) alkoxy group, (C1-C20) alkylthio, (C1-C20) alkoxycarbonyl or (C6-C20) ar (C1-C20) alkyl;

p and q are each independently 0 or an integer of 1 to 2; and $R_3$ and $R_4$ are each independently hydrogen or (C1-C20) alkyl.

2. The organic semiconductor compound of claim 1, wherein $Z_1$ and $Z_2$ are equally O, S, or Se;

$Y_1$ to $Y_4$ are each independently O, S, or Se;

$R_1$ and $R_2$ are each independently halogen, (C1-C20) alkyl, halo (C1-C20) alkyl or (C1-C20) alkoxycarbonyl;

p and q are each independently 0 or an integer of 1 to 2; and $R_3$ and $R_4$ are each independently (C1-C20) alkyl.

3. The organic semiconductor compound of claim 1, wherein the organic semiconductor compound is represented by Chemical Formula 2 below:

[Chemical Formula 2]

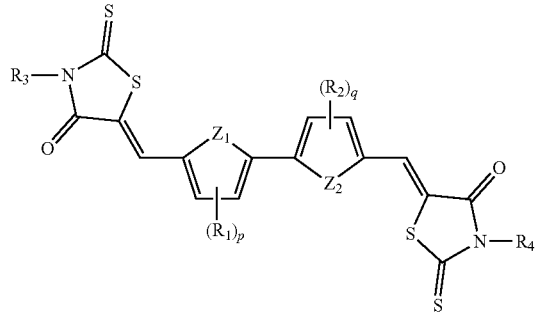

in Chemical Formula 2, $Z_1$ and $Z_2$ are each independently O, S, or Se;

$R_1$ and $R_2$ are each independently halogen, (C1-C20) alkyl, halo (C1-C20) alkyl or (C1-C20) alkoxycarbonyl;

p and q are each independently 0 or an integer of 1 to 2; and $R_3$ and $R_4$ are each independently (C1-C20) alkyl.

4. The organic semiconductor compound of claim 3, wherein $Z_1$ and $Z_2$ are the same as each other, and are O, S, or Se.

5. The organic semiconductor compound of claim 3, wherein the organic semiconductor compound is selected from the following compounds:

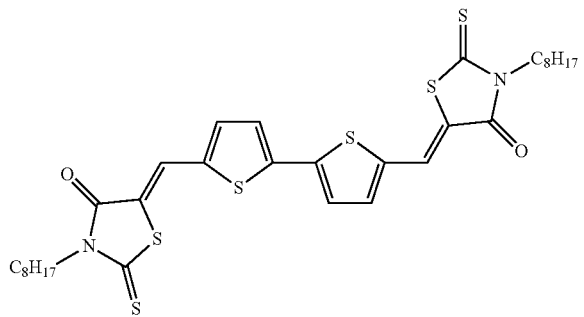

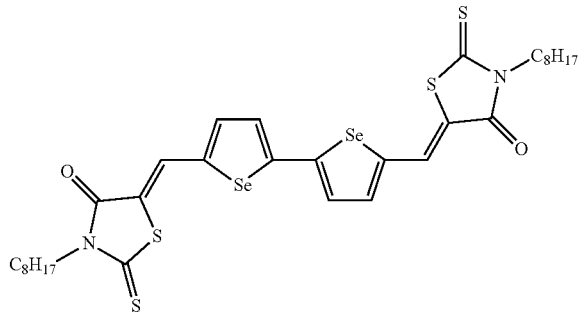

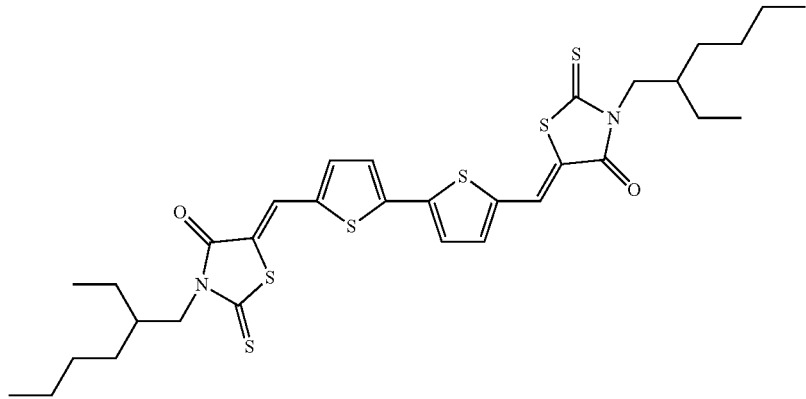

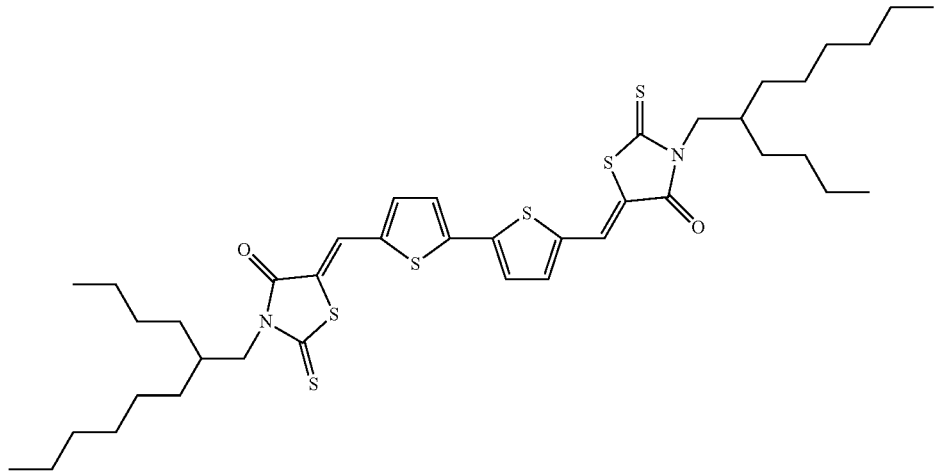

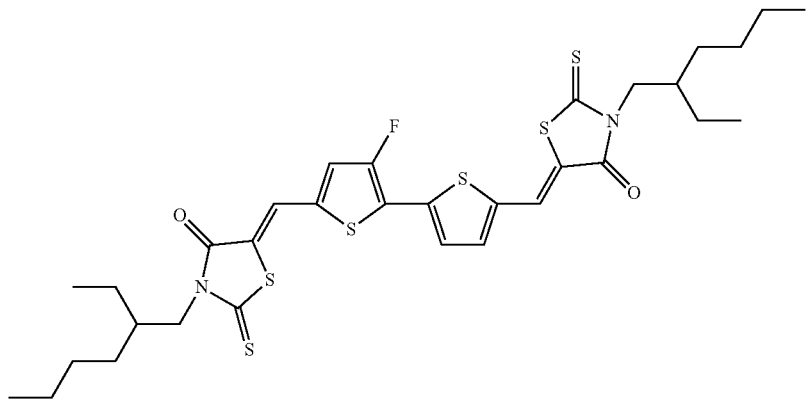
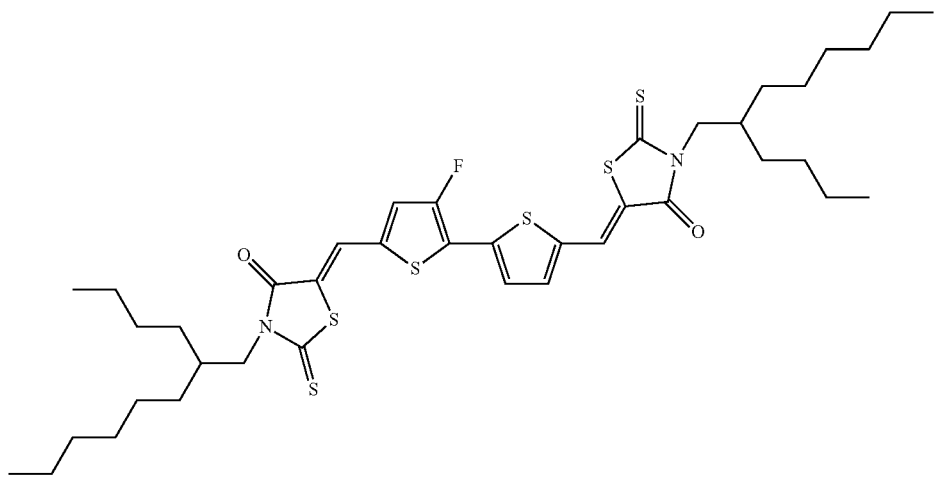
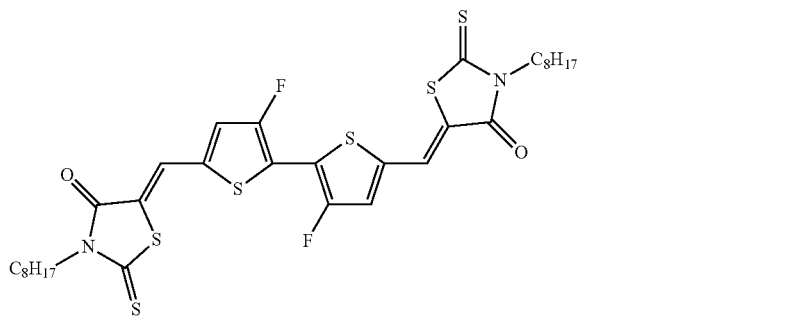
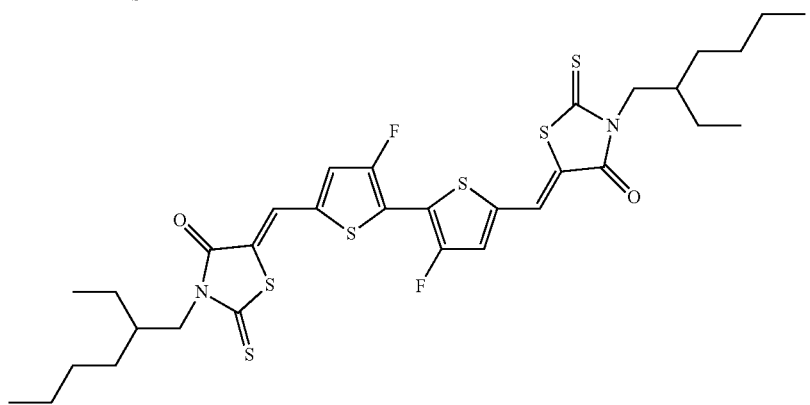

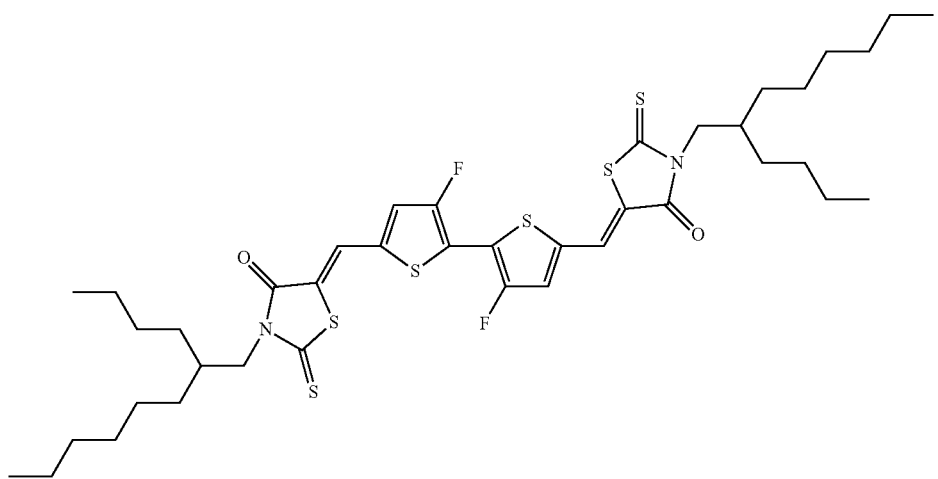
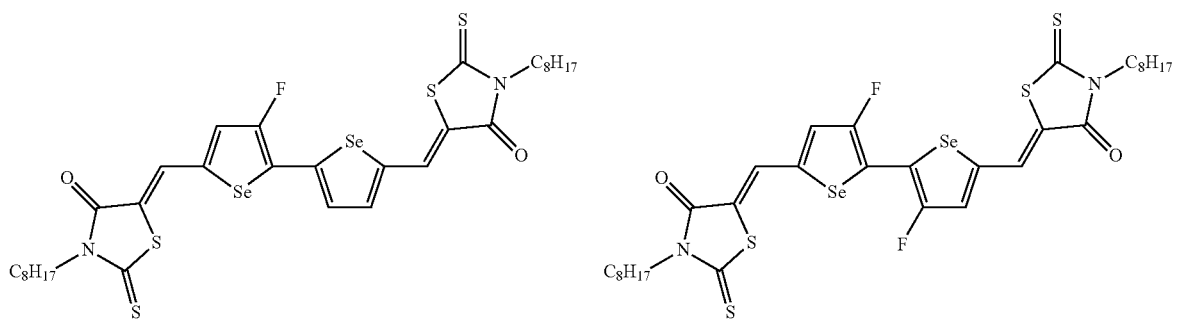
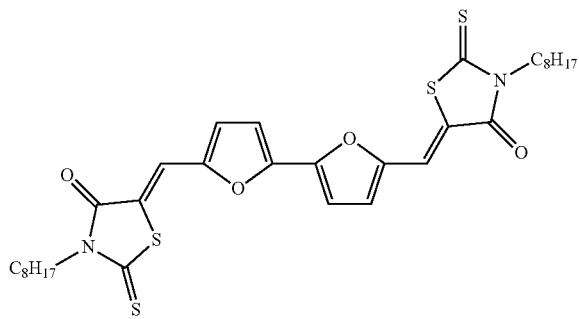
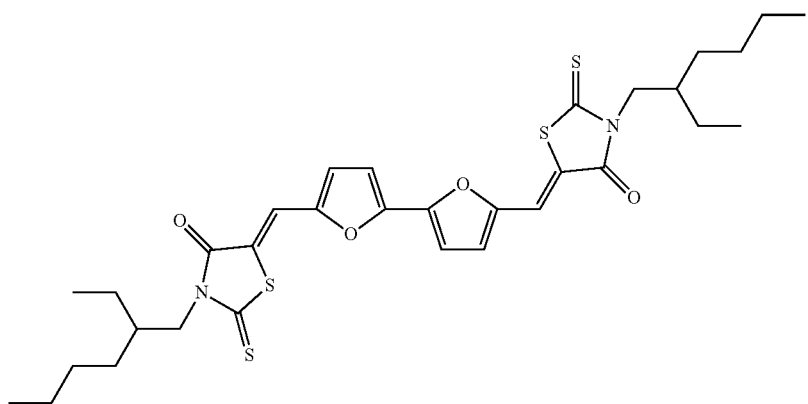 [SMILES: CCCCC(CC)CN1C(=O)/C(=C/c2ccc(-c3ccc(/C=C4\SC(=S)N(CC(CC)CCCC)C4=O)o3)o2)SC1=S]

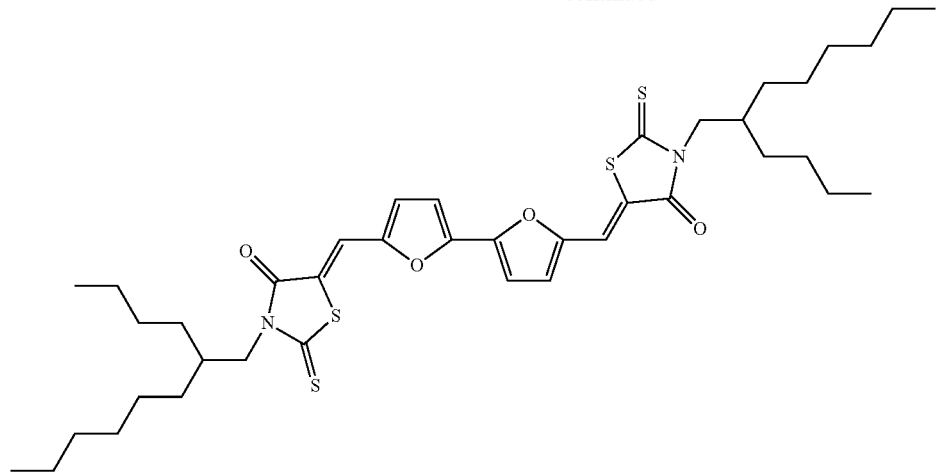
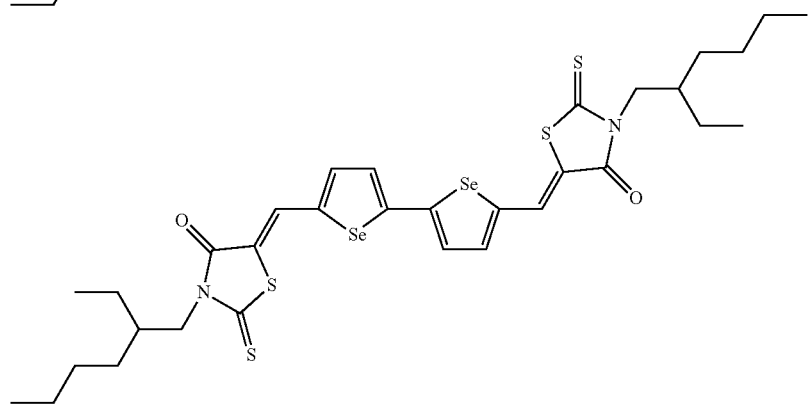
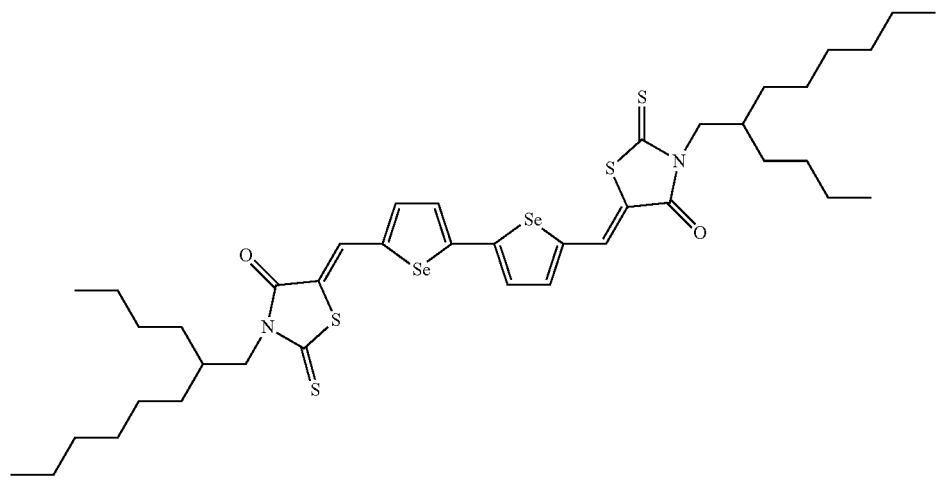 [SMILES: CCCCCCC(CCCC)CN1C(=O)/C(=C/c2ccc(-c3ccc(/C=C4\SC(=S)N(CC(CCCC)CCCCCC)C4=O)[se]3)[se]2)SC1=S]
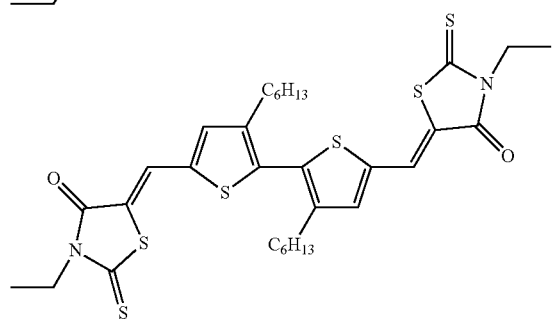

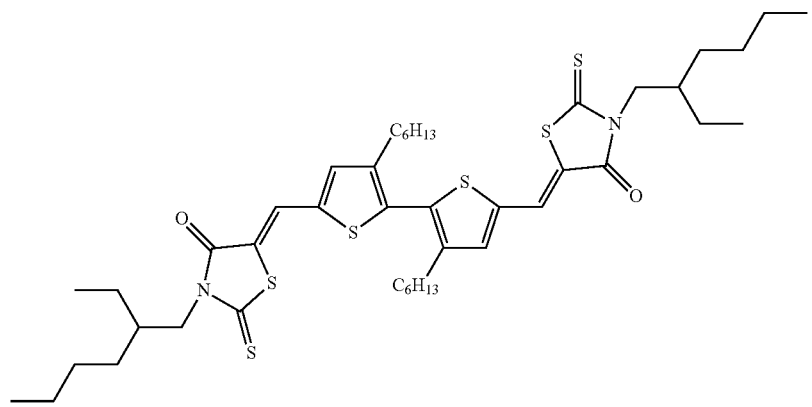
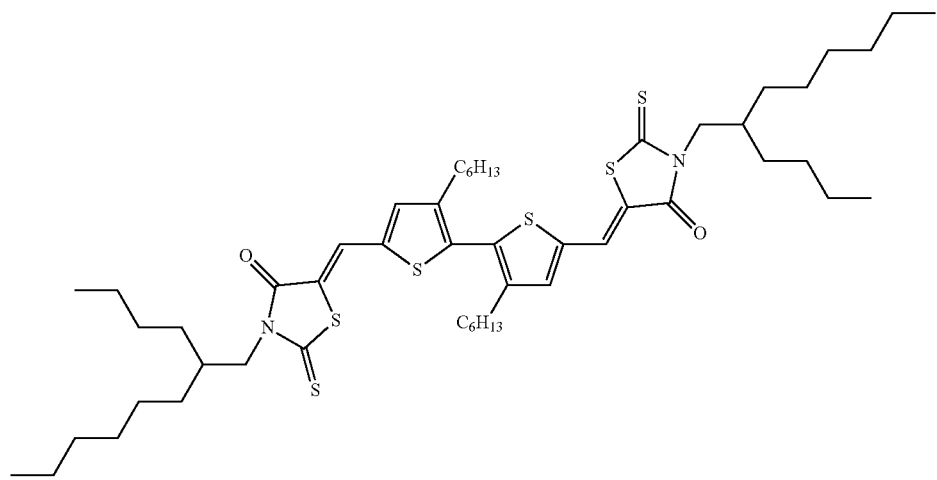
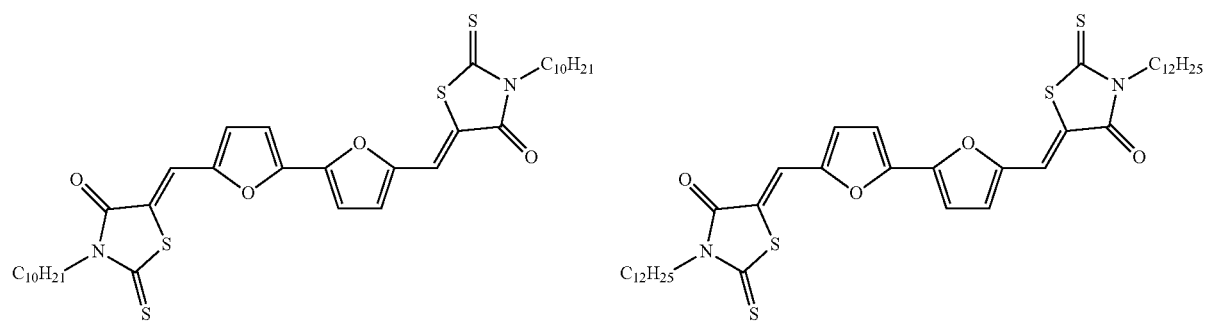
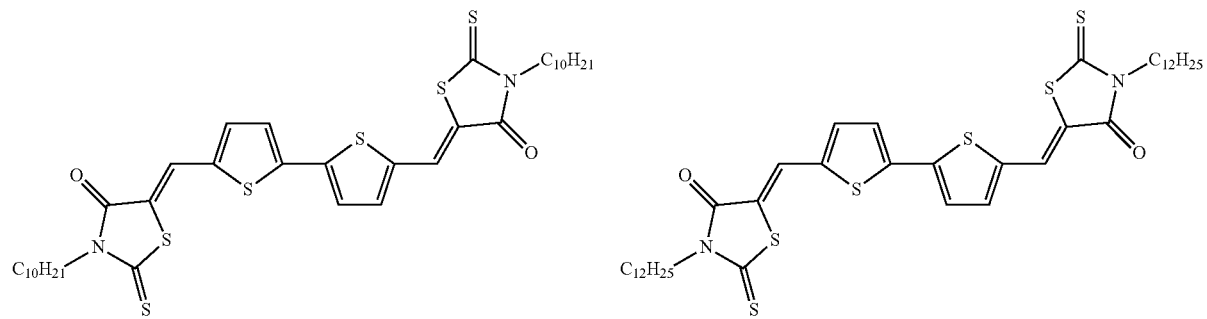

-continued
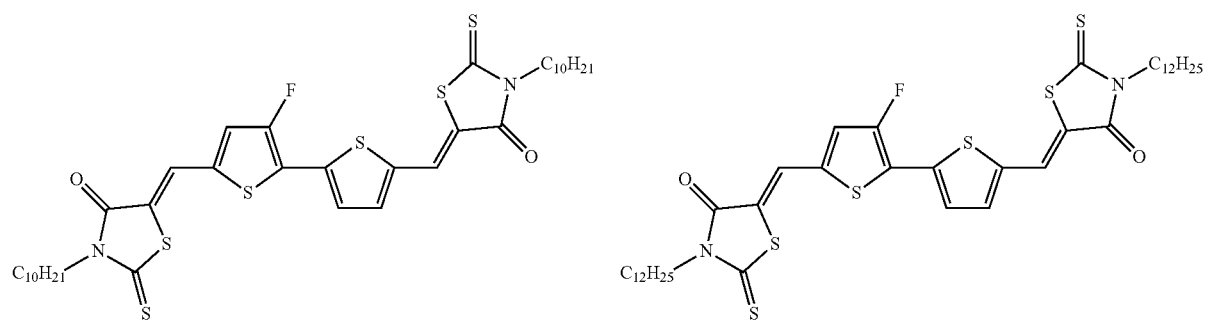
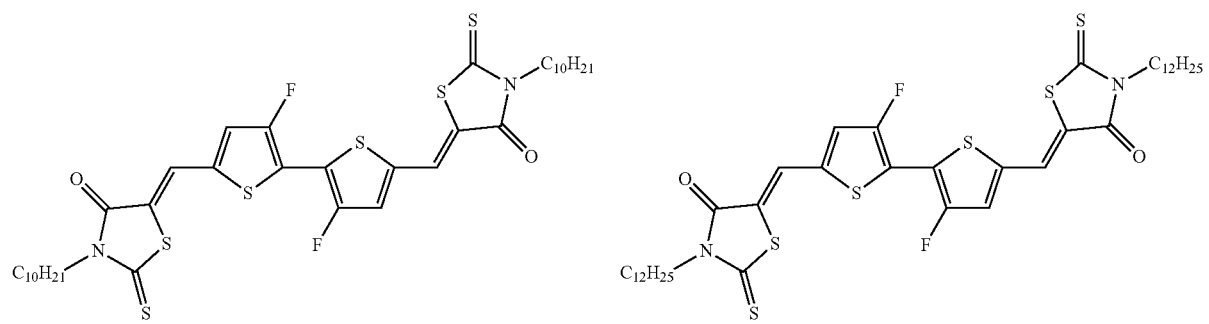
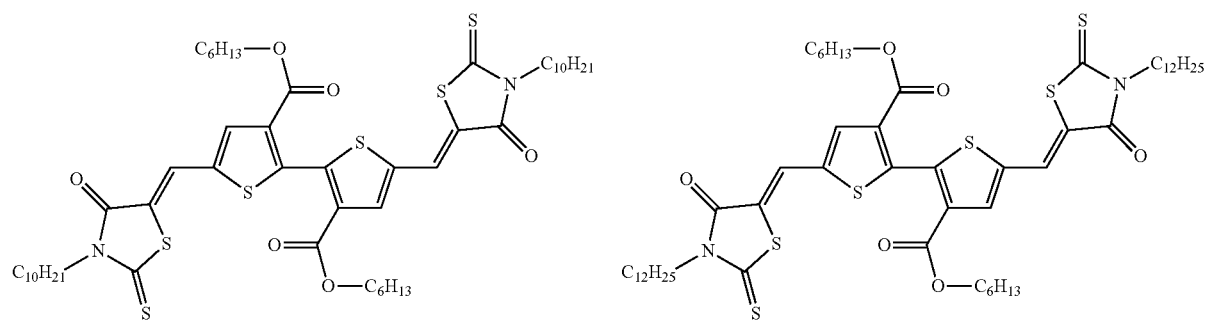
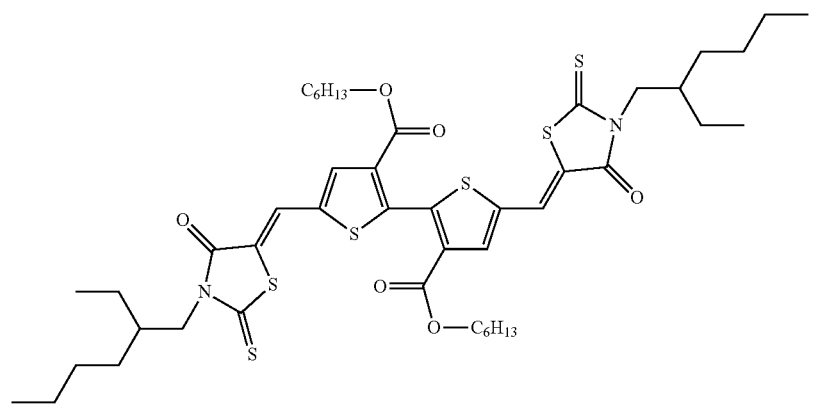

79
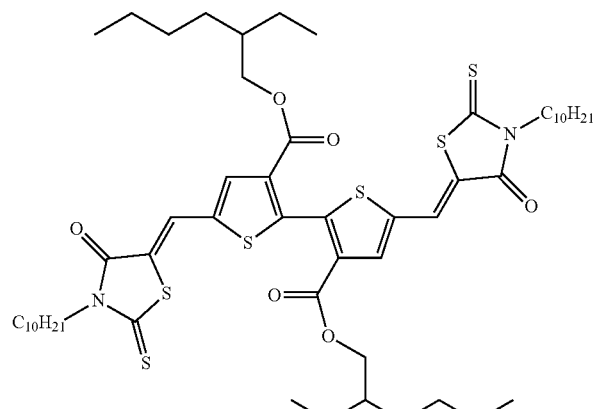
80
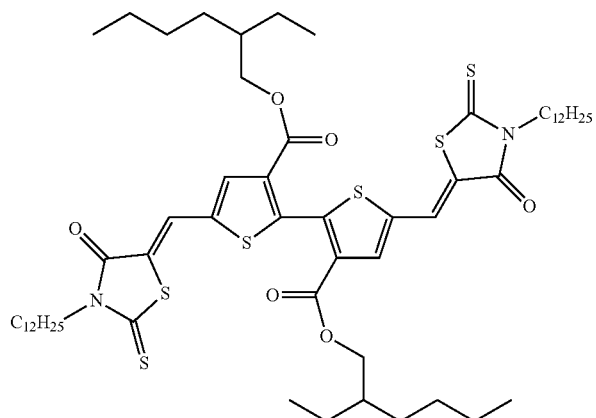
-continued
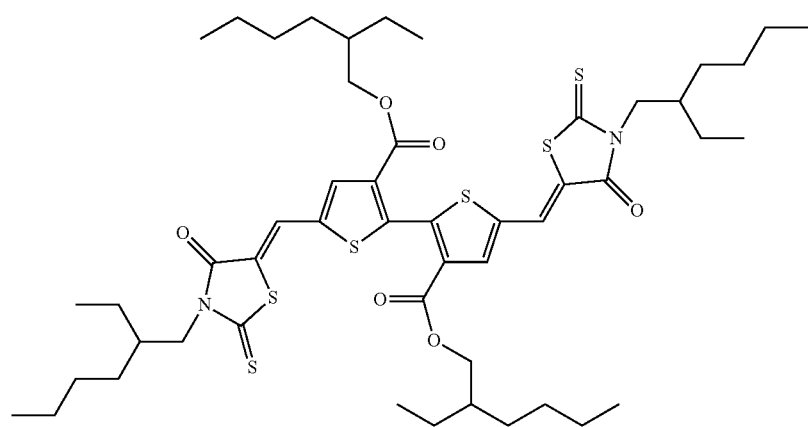
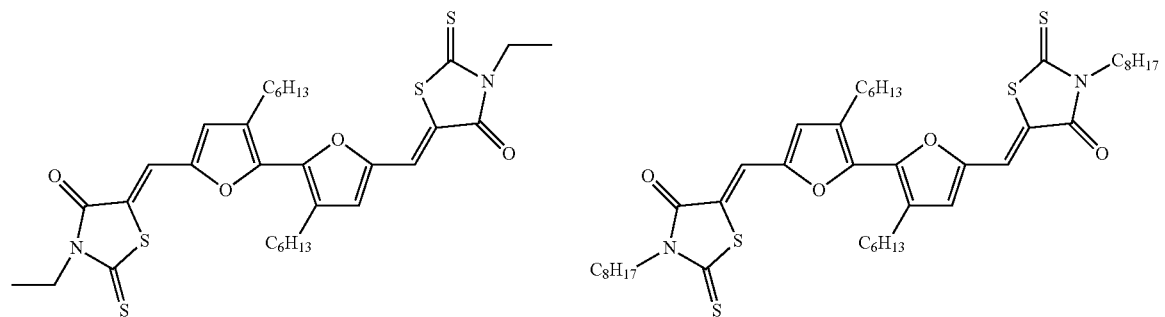
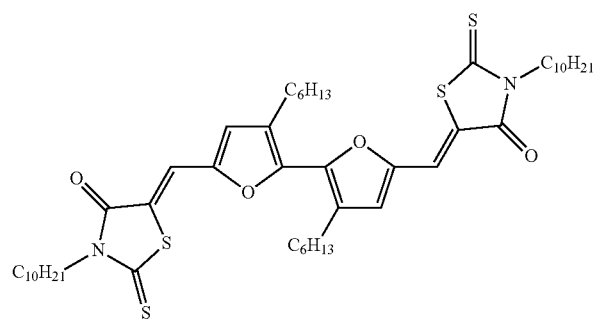
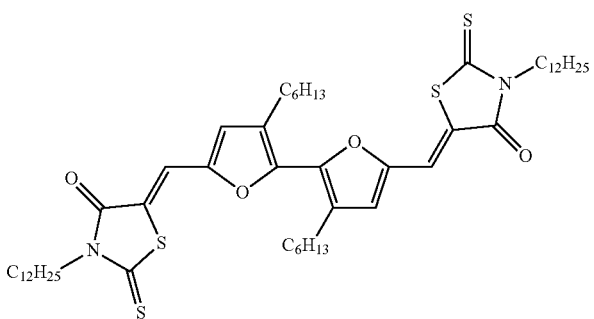

-continued
81
82
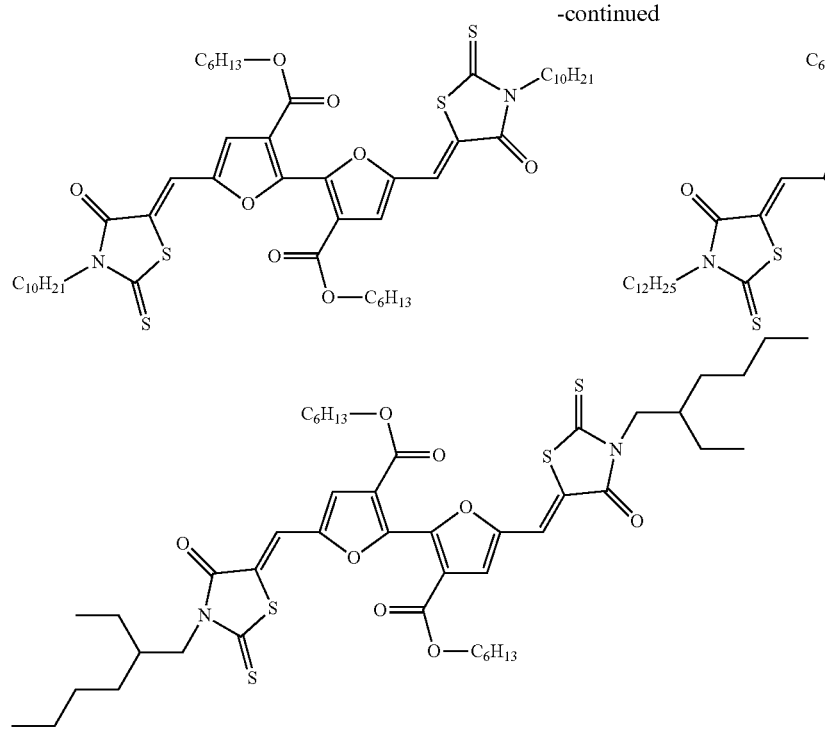
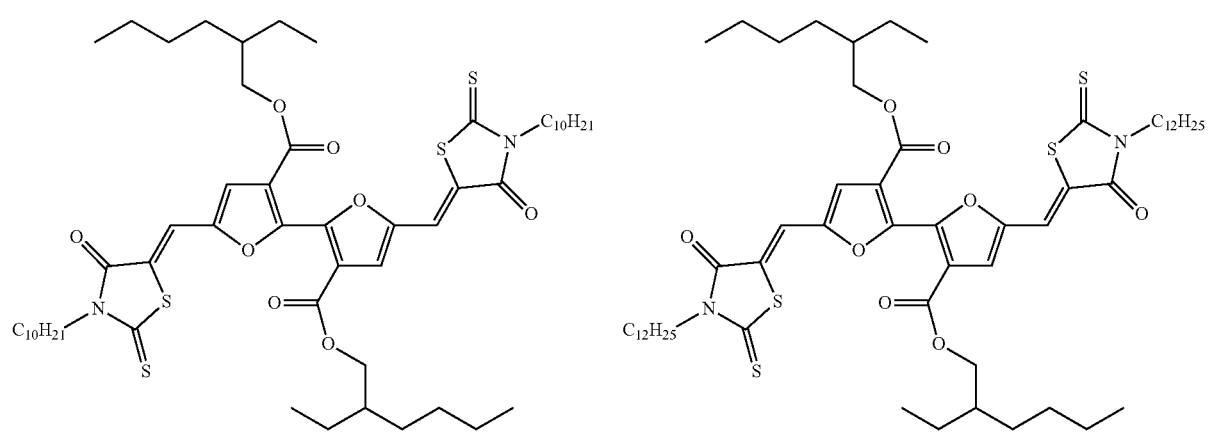
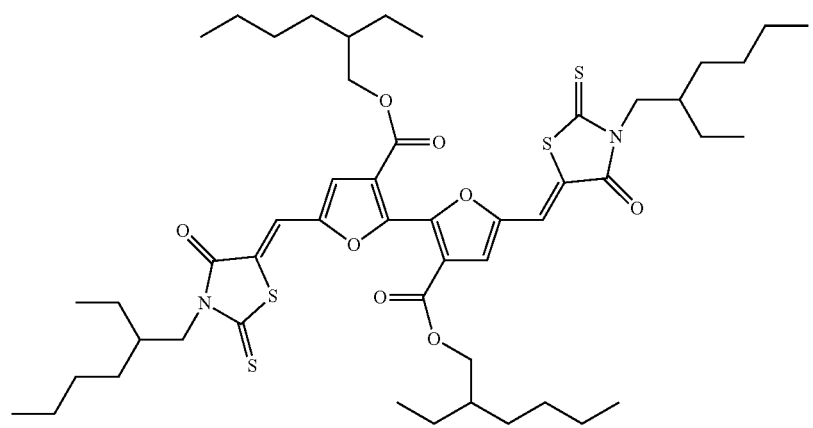

6. A production method of an organic semiconductor compound comprising:

producing an organic semiconductor compound represented by Chemical Formula 1 below by reacting a dicarbaldehyde compound represented by Chemical Formula 3 below, a thiazolidine compound represented by Chemical Formula 4 below, and a thiazolidine compound represented by Chemical Formula 5 below:

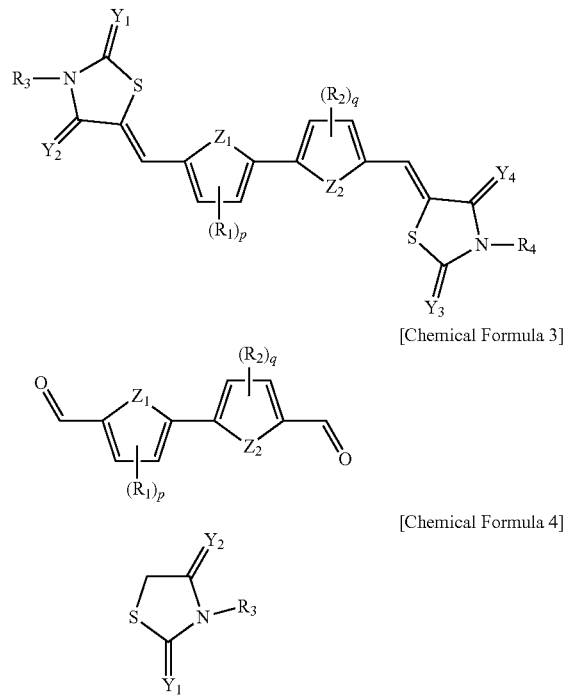

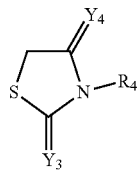

[Chemical Formula 5]

in Chemical Formulas 1, 3 to 5, $Z_1$ and $Z_2$ are each independently O, S, or Se;

$Y_1$ to $Y_4$ are each independently O, S, Se or $CR^aR^b$, and $R^a$ and $R^b$ are each independently cyano, a carboxyl group, (C1-C20) alkyl, (C1-C20) alkoxy or (C1-C20) alkoxycarbonyl;

$R_1$ and $R_2$ are each independently halogen, (C1-C20) alkyl, halo (C1-C20) alkyl, (C1-C20) alkoxy, (C1-C20) alkylthio, (C1-C20) alkoxycarbonyl or (C6-C20) ar (C1-C20) alkyl;

p and q are each independently 0 or an integer of 1 to 2; and $R_3$ and $R_4$ are each independently hydrogen or (C1-C20) alkyl.

7. An organic electronic device comprising the organic semiconductor compound of claim 1.

8. The organic electronic device of claim 7, wherein the organic electronic device is an organic solar cell.

9. The organic electronic device of claim 8, wherein the organic semiconductor compound is included in a photoactive layer of the organic solar cell.

10. The organic electronic device of claim 9, wherein the organic semiconductor compound is used as an electron acceptor.

* * * * *